( 12 ) United States Patent
Rozgic et al.

(10) Patent No.: US 11,043,843 B2
(45) Date of Patent: Jun. 22, 2021

(54) LOAD ADAPTIVE, RECONFIGURABLE ACTIVE RECTIFIER FOR MULTIPLE INPUT MULTIPLE OUTPUT (MIMO) IMPLANT POWER MANAGEMENT

(71) Applicant: The Regents of the University of California, Oakland, CA (US)

(72) Inventors: Dejan Rozgic, Los Angeles, CA (US); Dejan Markovic, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/479,540

(22) PCT Filed: Jan. 22, 2018

(86) PCT No.: PCT/US2018/014723
§ 371 (c)(1),
(2) Date: Jul. 19, 2019

(87) PCT Pub. No.: WO2018/136885
PCT Pub. Date: Jul. 26, 2018

(65) Prior Publication Data
US 2019/0379239 A1 Dec. 12, 2019

Related U.S. Application Data

(60) Provisional application No. 62/448,850, filed on Jan. 20, 2017.

(51) Int. Cl.
*H02J 50/10* (2016.01)
*A61N 1/378* (2006.01)
(Continued)

(52) U.S. Cl.
CPC ............ *H02J 50/10* (2016.02); *A61N 1/3787* (2013.01); *H02J 7/0068* (2013.01); *H02J 7/025* (2013.01)

(58) Field of Classification Search
CPC .......... H02J 50/10; H02J 7/0068; H02J 7/025; A61N 1/3787; A61N 1/025; A61N 1/0534;
(Continued)

(56) References Cited

U.S. PATENT DOCUMENTS

| 2004/0039423 | A1* | 2/2004 | Dolgin | A61N 1/37223 607/27 |
| 2005/0288739 | A1* | 12/2005 | Hassler, Jr. | A61N 1/3787 607/61 |
| 2017/0031441 | A1* | 2/2017 | Muller | A61B 5/24 |

FOREIGN PATENT DOCUMENTS

| EP | 3570934 A1 | 11/2019 |
| WO | 2015120324 A1 | 8/2015 |
| WO | 2018136885 A1 | 7/2018 |

OTHER PUBLICATIONS

Li Et Al., "A 13.56 MHz Wireless Power Transfer System With Reconfigurable Resonant Regulating Rectifier and Wireless Power Control for Implantable Medical Devices", IEEE Journal of Solid-State Circuits, vol. 50, No. 4, Apr. 1, 2015, pp. 978-989. (Year: 2015).*

(Continued)

*Primary Examiner* — Jared Fureman
*Assistant Examiner* — Michael J Warmflash
(74) *Attorney, Agent, or Firm* — KPPB LLP

(57) ABSTRACT

Many embodiments provide an implant power management unit (IPMU) that includes a reconfigurable active rectifier (AR) for wireless power transfer (WPT), where the AR is configurable to operate in a plurality of different modes of operation, an adaptive load control (ALC) unit that accom- (Continued)

modates power delivery with load requirements, where the ALC unit is configured to control AR voltage based upon a desired value, control circuitry that is configured to enable a full bridge rectifier in a regular mode of operation of the AR, a feedback circuit that adaptively generates offset current to compensate for switch delays in at least one active NMOS diode, and a feedback circuit that adaptively generates offset current to compensate switch delays in at least one active PMOS diode.

20 Claims, 24 Drawing Sheets

(51) Int. Cl.
  *H02J 7/00*     (2006.01)
  *H02J 7/02*     (2016.01)
(58) Field of Classification Search
  CPC ..... A61N 1/36067; A61N 1/08; H02M 7/217; H02M 1/10
  See application file for complete search history.

(56) References Cited

OTHER PUBLICATIONS

Lee Et Al., "An Adaptive Reconfigurable Active Voltage Doubler/Rectifier for Extended-Range Inductive Power Transmission", IEEE Transactions on Circuits And Systems—II: Express Briefs, vol. 59, No. 8, Aug. 1, 2012, pp. 481-485. (Year: 2012).*

Chris Glaser: "The Voltage-mode, Hysteretic, Or Hysteretic-Based: Which To Choose?", , Jan. 6, 2014 (2014-01-06), XP055730549, (Year: 2014).*
International Preliminary Report on Patentability for International Application No. PCT/US2018/014723, Report dated Jul. 23, 2019, dated Aug. 1, 2019, 4 Pgs.
International Search Report and Written Opinion for International Application No. PCT/US2018/014723, Search dated Mar. 12, 2018, dated Apr. 23, 2018, 11 Pgs.
Extended European Search Report for European Application No. 18741615.1 Search completed Sep. 14, 2020, dated Sep. 24, 2020, 13 Pgs.
Cha et al., "A CMOS Rectifier With a Cross-Coupled Latched Comparator for Wireless Power Transfer in Biomedical Applications", IEEE Transactions on Circuits and Systems — II: Express Briefs, vol. 59, No. 7, Jul. 1, 2012, pp. 409-413.
Glaser, "Voltage-mode Hysteretic, or Hysteretic-Based: Which to Choose?", ElectronicDesign, Jan. 6, 2014, 6 pgs.
Huang et al., "A Near-Optimum 13.56 MHz Cmos Active Rectifier With Circuit-Delay Real-Time Calibrations for High-Current Biomedical Implants", IEEE Journal of Solid-State Circuits, vol. 51, No. 8, Aug. 1, 2016, pp. 1797-1809.
Lee et al., "A High Frequency Active Voltage Doubler in Standard CMOS Using Offset-Controlled Comparators for Inductive Power Transmission", IEEE Transactions on Biomedical Circuits and Systems, vol. 7, No. 3, Jun. 1, 2013, pp. 213-224.
Lee et al., "An Adaptive Reconfigurable Active Voltage Doubler/Rectifier for Extended-Range Inductive Power Transmission", IEEE Transactions on Circuits And Systems—II: Express Briefs, vol. 59, No. 8, Aug. 1, 2012, pp. 481-485.
Li et al., "A 13.56 MHz Wireless Power Transfer System With Reconfigurable Resonant Regulating Rectifier and Wireless Power Control for Implantable Medical Devices", IEEE Journal of Solid-State Circuits, vol. 50, No. 4, Apr. 1, 2015, pp. 978-989.

* cited by examiner

MIMO Implant Power Management - Different Mode of Operation

*Power Management Unit – Wired Mode*

Active diodes current waveforms without delay compensation

Detailed schematic of the real-time, adaptive on/off delay compensation technique for NMOS active diode Timing diagram for NMOS active diode driver Control logic for AR-WPT reconfigurable system Near-Optimum Steady-state for Regular (2X) and Charging Mode(2X). *Simulated waveforms – desired timing*

Waveforms for PMOS active diode with on/off offset control a) Stimulation + Full-Fledged Power Management Unit IC b) System-level Integration – Example of Neuromodulation (NM) Unit

LOAD ADAPTIVE, RECONFIGURABLE ACTIVE RECTIFIER FOR MULTIPLE INPUT MULTIPLE OUTPUT (MIMO) IMPLANT POWER MANAGEMENT

CROSS REFERENCE TO RELATED APPLICATIONS

This application is a national stage of PCT Patent Application No. PCT/US2018/014723, entitled "Load Adaptive, Reconfigurable Active Rectifier for Multiple Input Multiple Output (MIMO) Implant Power Management" to Rozgic et al., filed Jan. 22, 2018, which claims priority to U.S. Provisional Application No. 62/448,850, entitled "Load Adaptive, Reconfigurable Active Rectifier for Multiple Input Multiple Output (MIMO) Implant Power Management" to Rozgic et al., filed Jan. 20, 2017, the disclosures of which are incorporated by reference herein in their entirety.

STATEMENT OF FEDERALLY SPONSORED RESEARCH

This invention was made with Government support under Grant Number 20163328, awarded by the Defense Advanced Research Projects Agency. The Government has certain rights in this invention.

FIELD OF THE INVENTION

The present invention generally relates to implantable biomedical devices, in particular to implant power management units (IPMUs) that are highly programmable and that can process multiple input power deliveries on-the-chip.

BACKGROUND

There has been great interest in the neuroscience community in decoding the functioning of the brain. Neuromodulation, e.g. deep-brain stimulation (DBS), provides symptomatic relief to neurological disease by emitting pulses to overcome abnormal brain activity. It is efficacious in Parkinson's disease and other movement disorders, which are anatomically focal, where open-loop stimulation on just one contact is sufficient. The same technology doesn't show therapeutic benefit in network-scale indications such as depression or Alzheimer's disease, where a more precise localization as well as distributed sensing and stimulation are necessary. Also, continuous open-loop stimulation can be harmful and it can lose efficacy over time because of the changes in the brain. Further, modern neuroscience is attempting to "close the loop" with the brain, by stimulating specific areas using current pulses, and recording neuronal responses to learn and adapt the stimulation patterns. For example, it has been demonstrated in a limited number of patients that stimulating certain regions of the entorhinal cortex of the brain could improve memory function.

SUMMARY OF THE INVENTION

Implant power management units in accordance with various embodiments of the invention are disclosed. In one embodiment, an implant power management unit (IPMU) includes a reconfigurable active rectifier (AR) for wireless power transfer (WPT), where the AR is configurable to operate in a plurality of different modes of operation, an adaptive load control (ALC) unit that accommodates power delivery with load requirements, where the ALC unit is configured to control AR voltage based upon a desired value, control circuitry that is configured to enable a full bridge rectifier in a regular mode of operation of the AR, a feedback circuit that adaptively generates offset current to compensate for switch delays in at least one active NMOS diode, and a feedback circuit that adaptively generates offset current to compensate switch delays in at least one active PMOS diode.

In a further embodiment, the control circuitry is configured to enable two half-wave rectifiers connected in series in a charging mode of operation of the AR such that the AR-WPT operates as a voltage doubler.

In another embodiment, the IPMU further includes a battery, where the AR-WPT includes a differential AC input, and where the charging mode is enabled during recharging of the battery by the IPMU and requires a higher input voltage swing than the input voltage swing of an input signal received at the AC input during the regular mode.

In yet a further embodiment, the feedback circuit further includes a comparator that is realized as a push-pull common-gate comparator.

In still a further embodiment, the push-pull common-gate comparator includes p-type input transistors.

In another embodiment again, the push-pull common-gate comparator includes n-type transistors.

In still another embodiment, the AR-WPT includes several comparators that drive the gates of power transistors within active diodes.

In still yet another embodiment again, the IPMU includes an offset calibration circuit configured to generate offset currents for the comparators in the AR-WPT.

In yet another embodiment still, the AR-WPT includes five power switches, three adaptive delay compensated comparators with two driving an NMOS diode and one driving a PMOS diode.

In another embodiment again, the ALC unit includes a Hysteretic Comparator (HC)

In another embodiment yet again, the HC is connected to a 2-stage amplifier by employing a resistor of fixed value together with a steering circuit, where the amplifier's negative input terminal is shifted by a value proportional to the product of the resistor and a hysteresis bias current output by the HC.

In a further embodiment again still, the IPMU operates in a wired mode where power is delivered differentially through a plurality of wires.

In a still further embodiment again, the IPMU operates in a wireless mode where power is delivered through a near-field inductive link.

In still a further embodiment again, the IPMU operates in wireless mode where power is delivered through an inductive link while simultaneously charging a rechargeable battery.

In still a further embodiment again still, the IPMU operates in battery mode where power is supplied from a battery.

In another embodiment again, the IPMI further includes a scalable bandgap reference current block (BGR/IR) and several voltage generators for several implant units.

In still a further embodiment again, the IPMU further includes two wires at an input that carry sinusoidal signals shifted for 180 degrees such that the net input voltage sum in the two wires is equal to zero.

In still a further embodiment again, the IPMU further includes a duty-cycle control unit used as a shunt regulator that adapts power delivery to the load and sets the active rectifier output voltage to a desired value.

In still another further embodiment again, an active diode inputs two control signals for transitioning from passive to active mode and for preventing excessive power dumping to the load.

In yet still a further embodiment again, the IPMU further includes an active body biasing scheme (ABB) that connects the bulk of each power transistor to a higher potential node.

DETAILED DESCRIPTION

Turning now to the drawings, implant power management units (IPMUs) in accordance with various embodiments of the invention are illustrated. In particular, many embodiments provide a full-fledged IPMU that is able to minimize the power consumption of a fully implantable biomedical device and to make the stimulator design compatible with the rest of the system, that is as an integrative part of the STIM chip (as a part of neuromodulation unit). In many embodiments, the IPMU is highly reconfigurable and can process and support different power transfers on-the-chip depending on the application. In several embodiments, the IPMU unit is made in high-voltage (HV) technology to accommodate large voltage swings at the electrodes during stimulation. As a part of an IPMU's specification, several important targets may be defined including the following: i) the IPMU should adapt the power delivery depending on the need at the load, ii) the IPMU should provide multiple modes of operation and smooth transitioning between the modes iii) the IPMU should provide high power conversion efficiency (e.g., PCE>90%), and iv) the IPMU should utilize a small chip area and few off-chip components to satisfy low cost and small volume (implantable interface) requirements.

Figure 1:
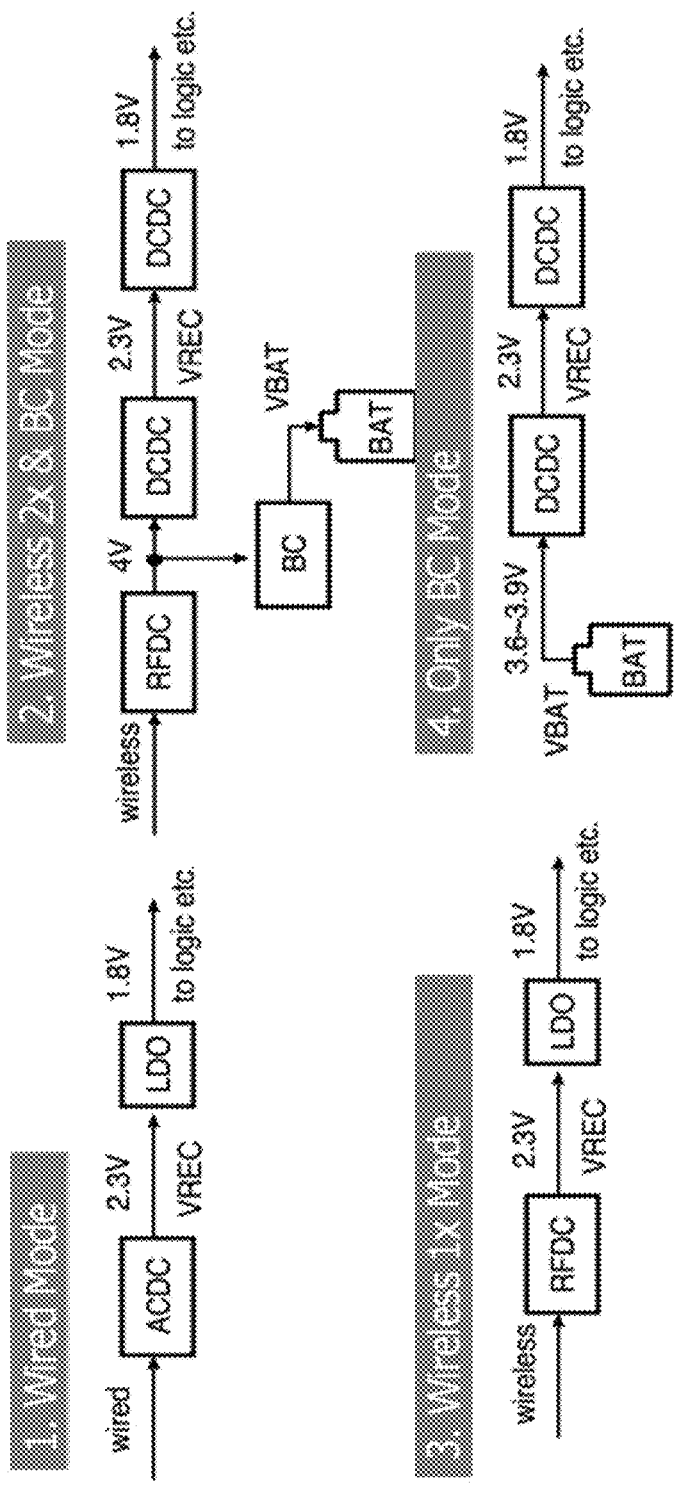
FIG. 1 illustrates an implant power management unit (IPMU) that supports different modes of operation in accordance with an embodiment of the invention.

In many embodiments, an IPMU may support four different modes of operation and can be controlled by six control signals that are set through a Digital Control Unit (DCU) and a user interface. An example of an IPMU that supports four different modes of operation in accordance with an embodiment of the invention is illustrated in FIG. 1. The four modes of operation may include 1) wired mode, 2) wireless 2× & battery (BC) mode, 3) wireless 1× mode, and 4) only BC mode.

As illustrated in FIG. 1, the IPMU system can be configured to work in 1) wired mode where the power is delivered to the implant differentially through two wires; 2) wireless 1× mode where the power is delivered through a near-field inductive link; 3) wireless 2× mode in which power is delivered through an inductive link while simultaneously the rechargeable battery is charging and the implant is powered; and 4) battery mode where the whole implant is supplied from the battery. Although FIG. 1 illustrates an IPMU that can support four different modes of operation, an IPMU may be designed to support any of a variety of modes of operation, including a single mode of operation or any of a plurality of modes of operation as required by the requirements of specific applications in accordance with embodiments of the invention. MIMO implant power management systems for biomedical applications are discussed further below.

Figure 2:
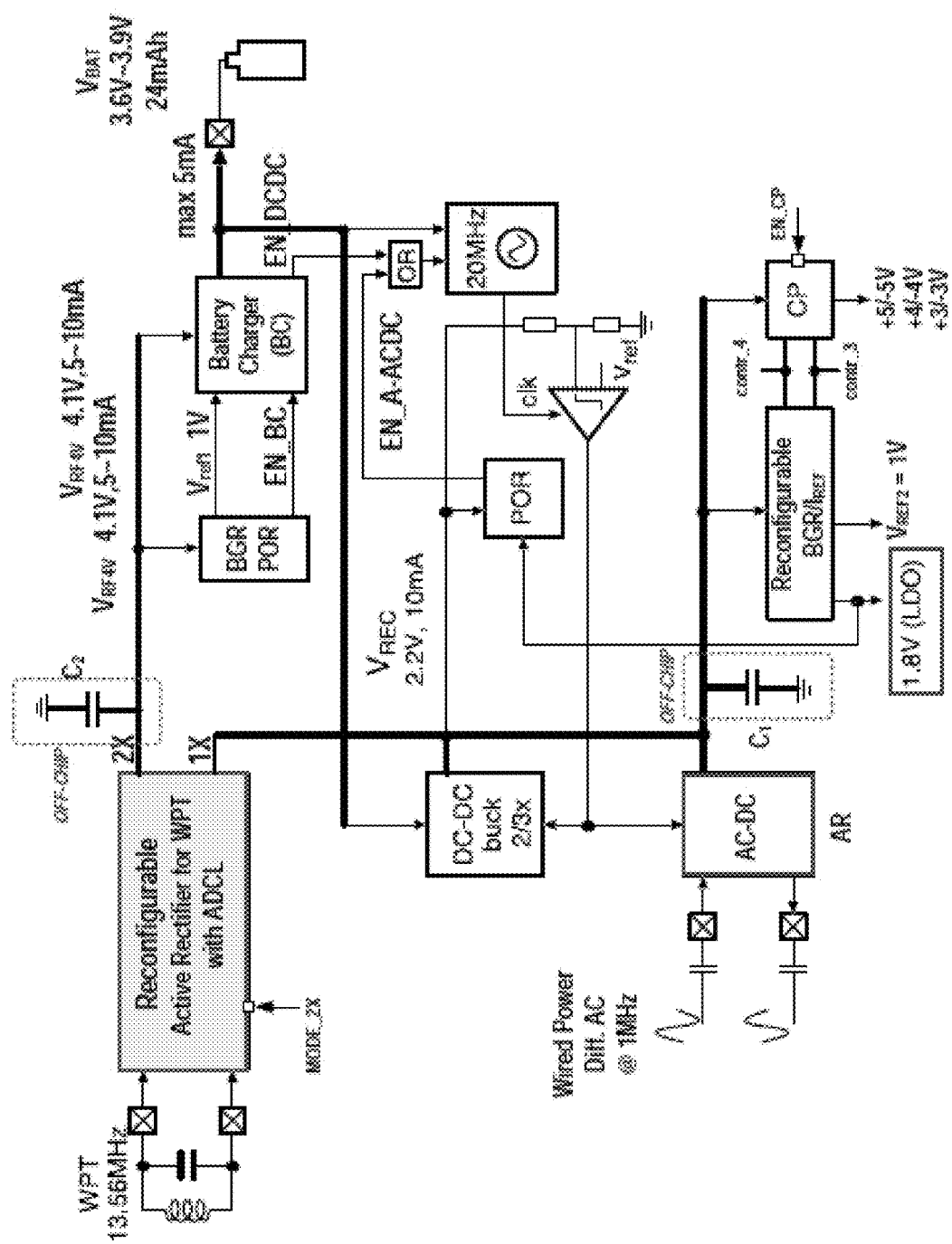
FIG. 2 illustrates a block diagram of a full-fledged IPMU in accordance with an embodiment of the invention.

An example of a complete block diagram of a full-fledged IPMU in accordance with an embodiment of the invention is illustrated in FIG. 2. As illustrated in FIG. 2, the IPMU includes a reconfigurable active rectifier. In many embodiments, as the most power greedy blocks, efficient active rectifiers for both wired and wireless power transfer may be imperative and are discussed in detail below.

To improve the overall efficiency and maintain the efficacy of the neuromodulation (NM) interface of the inductively/wireline supplied stimulating medical devices, the efficiency of every stage in the power delivery path, such as the active rectifiers, high voltage generators, inductive link, among various others, should be maximized. By adopting a system level approach and utilizing power-efficient circuit techniques for both TX and RX side, many embodiments provide an IPMU that outperforms the current state-of-the-art in flexibility and efficiency, as discussed in detail below. Although FIG. 2 illustrates a particular architecture for a MIMO Implant Power Management System for biomedical applications, any of a variety of architectures may be specified as appropriate to the requirements of specific applications in accordance with embodiments of the invention.

Active Rectifier for Differential Wired Mode

Figure 3:
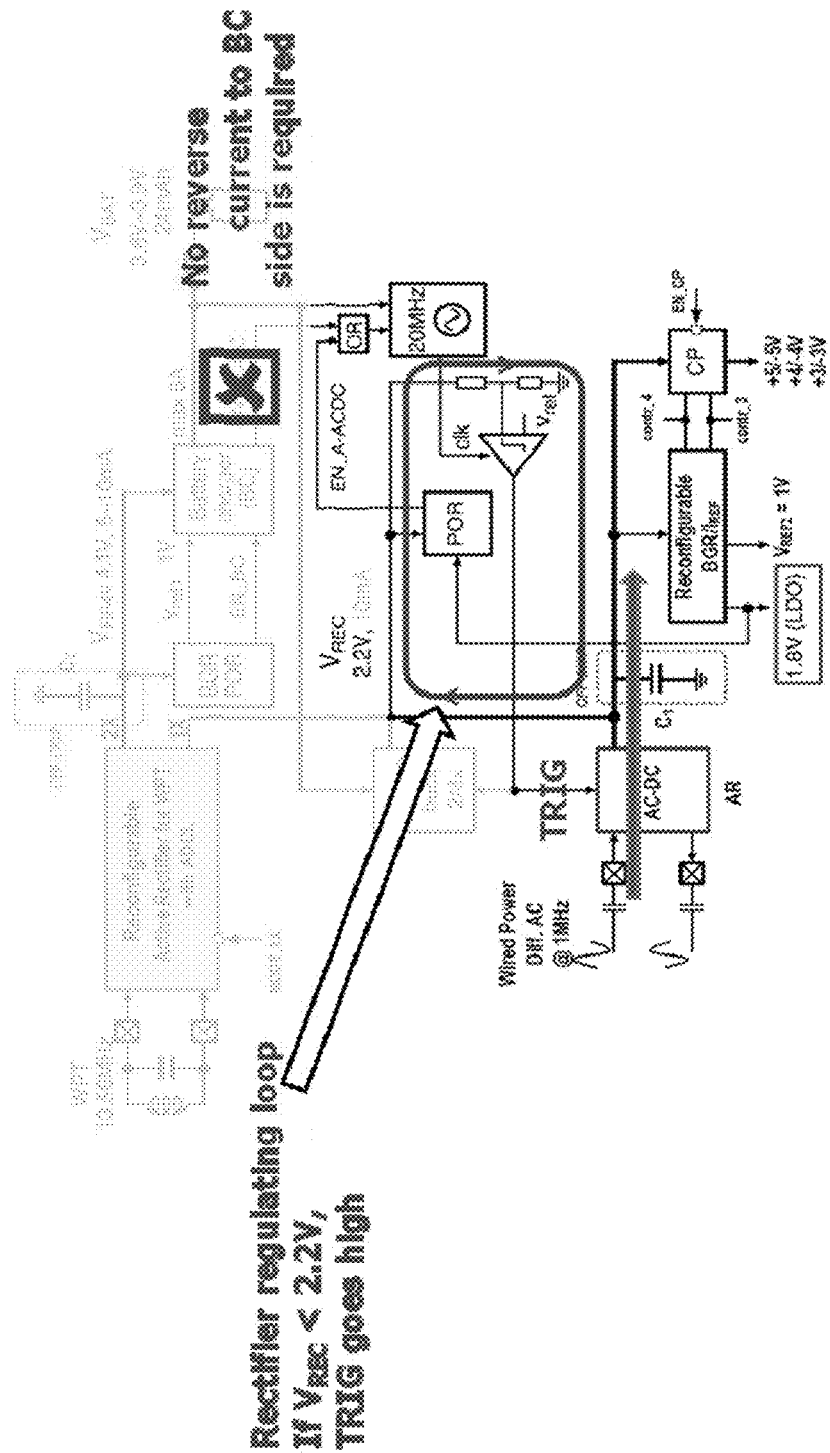
FIG. 3 illustrates an IPMU in wired mode in accordance with an embodiment of the invention.

In many embodiments of the IPMU, during operation in wired mode, a power management (PM) block can be configured automatically and wireless power transfer and battery management units can be turned-off so that there is no reverse current flow. An example of an IPMU in wired mode in accordance with an embodiment of the invention is illustrated in FIG. 3. As illustrated in FIG. 3, the implant can be powered by a differential AC input and an active IMPU can include an active rectifier (AR-DC), scalable bandgap/reference current block (BGR/IR) and multiple-voltage generators for the various implant units. Two wires at the input can carry sinusoidal signals shifted for 180 degrees to satisfy biomedical requirements so that the net input voltage sum in the wires is equal to zero at every moment in time. Peak-to-peak voltage can be 6V at each wire. A duty-cycle control unit can play the role of a shunt regulator that adapts the power delivery to the load and also sets the rectifier output voltage to the desired value—which in the embodiment illustrated in FIG. 3 is 2.2V. Although FIG. 3 illustrates a particular architecture of an IPMU in wired mode, any of a variety of architectures may be utilized as appropriate to the requirements of specific applications in accordance with embodiments of the invention.

Figure 4:
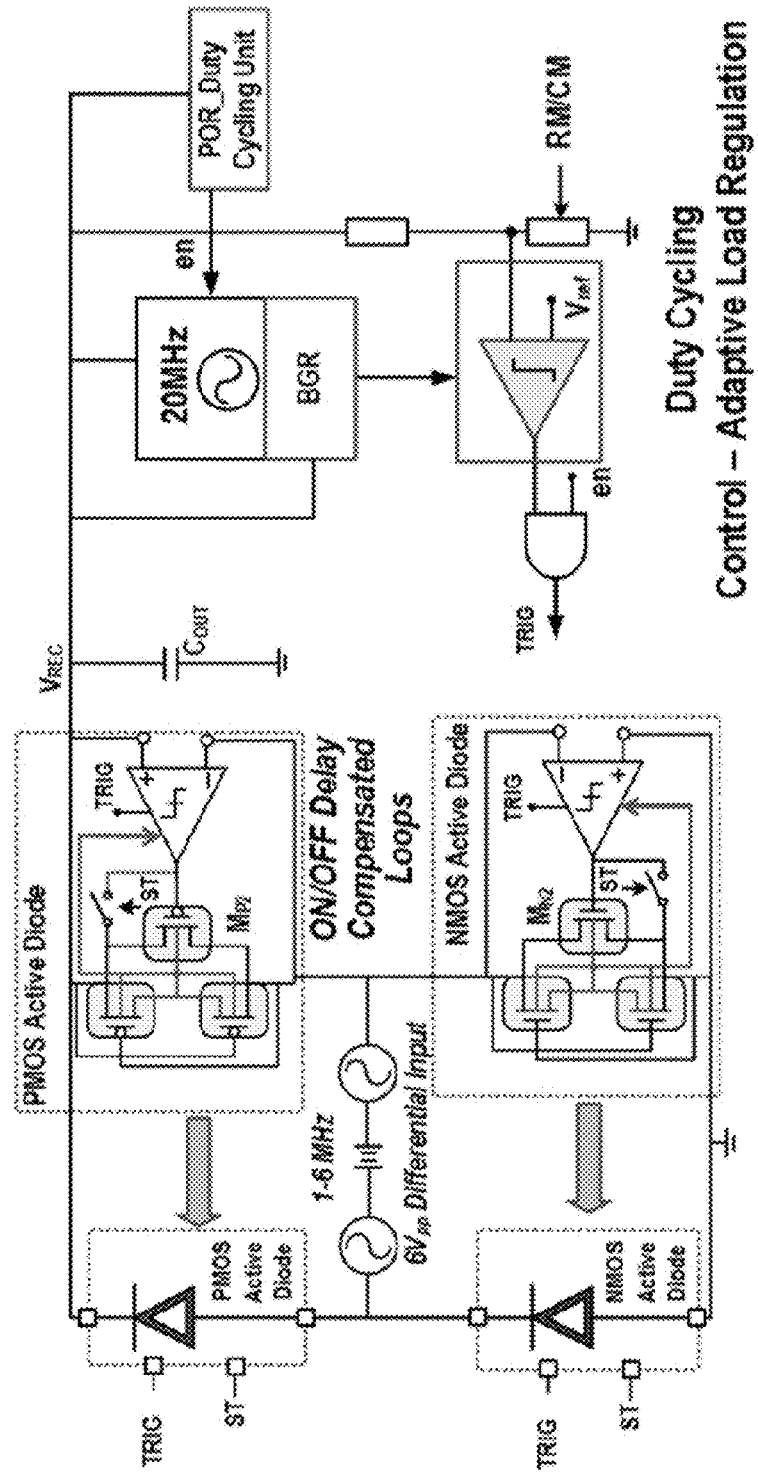
FIG. 4 illustrates an adaptive, real-time on/off delay-compensated active rectifier (AR) whose efficiency is improved and optimized for MHz-level inputs in accordance with an embodiment of the invention.

An adaptive, real-time on/off delay-compensated AR whose efficiency is improved and optimized for MHz-level inputs (PCE>80%) in accordance with an embodiment of the invention is illustrated in FIG. 4. In many embodiments, AR-DC also mitigates the substrate ringing and di/dt noise due to bondwire inductance. Output of the AR may supply the 1.8V LDO with high slew-rate and supply rejection. This LDO can power both ICs.

In many embodiments, in the core of the active rectifier for differential wired power transfer is a full-bridge architecture. In several embodiments, every Active Diode (AD) inputs two control signals, which may be necessary for transition from passive to active mode and for preventing excessive power dumping to the load. Also in certain embodiments, since the targeted rectified voltage is 2.2V and the amplitude of the input signal is 3V, the source (drain) of power PMOS/NMOS transistors within the AD can reach 4.1V in the steady state. If the drivers inside the AD are supplied from $V_{REC}$ and gnd, turning off these diodes becomes problematic. To handle this, many embodiments provide an active body biasing scheme (ABB), as illustrated in FIG. 4, to mitigate any current leakage and prevent reverse current flow, which connects the bulk of every power transistor to the higher potential node. At the same time, the bulk node can be used as a supply for the driver. The 1.1V offset can show up due to the isolation capacitances at the input of the active rectifier. Although FIG. 4 illustrates a particular active rectifier architecture for wired mode, any of a variety of architectures may be utilized as appropriate to the requirements of specific applications in accordance with embodiments of the invention.

Wireless Power Link

In many embodiments, for near-skin implantable biomedical devices, wireless power transfer (WPT) is a preferable power delivery option, which is usually based on the inductive near-field coupling due to its high efficiency. To be consistent with biomedical requirements, implantable applications usually use the frequencies from the ISM band, in which 13.56 MHz is the most commonly used carrier frequency. By employing WPT, scientists try to avoid bulky batteries, which is a critical demand in volume-limited applications where form factor plays a significant role. Since many embodiments of the IPMU target a fully-implantable, miniaturized NM platform, WPT is an important task.

In many embodiments, the Active Rectifier (AR) for the WPT is the most critical block regarding the power efficiency. In many embodiments, AR is designed to operate in two different modes: 1) Regular Mode (1×) which provides 2.2V rectified voltage which is sufficient for further voltage regulation and 2) Charging Mode (Doubling Mode-2×) which provides 4.1V output; this voltage can be used during the rechargeable battery charging. During 1× Mode, the AR architecture can be configured as a full-bridge rectifier, while during the 2× Mode it may be configured as a voltage doubler in which two half-wave rectifiers are connected in series.

Figure 5:
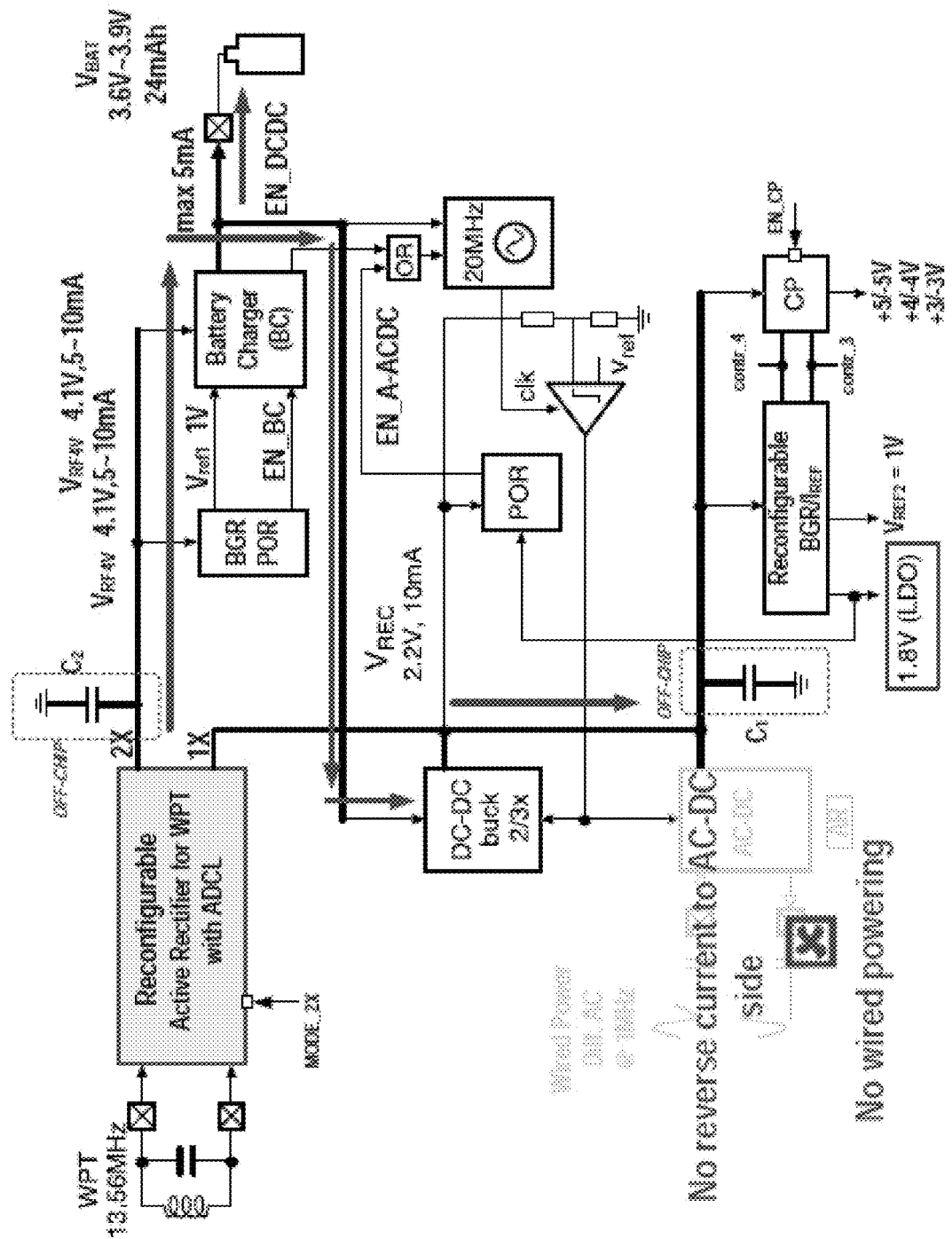
FIG. 5 illustrates enabled units in an IPMU during wireless power transfer (WPT) in Charging Mode in accordance with an embodiment of the invention

FIG. 5 illustrates enabled units in an IPMU during WPT in Charging Mode in accordance with an embodiment of the invention. As illustrated in FIG. 5, the battery charger (BC) may receive 4.1V at the input. In the illustrated embodiment, BC can charge the battery with 5-10 mA constant DC current. As can readily be appreciated, circuitry can be designed to receive any current appropriate to the requirements of a given application. Parallelly, integrated buck DC-DC converter may provide 2.2V to multiple LDOs and circuitry during normal implant operation. Most of the circuitry that is active during Wired Mode may be disabled and reverse current flow into the AC-DC rectifier prevented. Although FIG. 5 illustrates a particular full-fledged IPMU architecture in Charging Mode, any of a variety of IPMU architectures may be utilized as appropriate to the requirements of specific applications in accordance with embodiments of the invention.

In many embodiments, active realization of the AR-WPT benefits from high power efficiency and load adaptation ability. During the implant functioning, the load requirement may change in time—from very light to very high. Also coupling variations may significantly mitigate efficiency and make the output voltage unstable. Most previous designs do not consider the excessive power dumping from the input (wireless link) to the output. Excessive power can be either dumped to the DC-Limiter or absorbed by the body tissue. Usually, a simple DC-limiter circuit or clamping shunt regulator is employed to bound the $V_{REC}$ value. This may cause significant current leakage and it may mitigate the overall end-to-end efficiency. Since the load requirement may vary in the time, many embodiments provide a power efficient system with a dedicated adaptive load control unit that will accommodate power flow in regards to the implant requirements.

Accordingly, many embodiments provide a reconfigurable, PVT invariant and power efficient AR-WPT which includes an Adaptive Load Control (ALC) unit that accommodates the power delivery. With the ALC unit, input power can be controlled and excessive power at the output may be significantly reduced. The efficiency of the rectifier can be improved due to the new real-time offset controlled schemes that are implemented. With these two techniques, many embodiments of the system are able to perform >10× longer (battery life) compared to the state-of-the-art and have improved efficiency for a wide range of load currents.

In many embodiments, during design of active rectifiers for WPT that use 10's of MHz as a carrier frequency, an important drawback may need to be considered in relation to propagation delays which may be introduced by comparators (drivers). These drivers may be driving the gates of the power transistors within the active diodes. To have small voltage drops across the active diodes, these power transistors may need to be wide. The wider the transistors, the bigger their gate capacitance. To drive these capacitances at high speeds, the comparators may require a buffer chain in the output stage. Naturally, there may be a delay between changing the state at the comparator input and the buffer chain output. This delay may cause power transistors to turn-on/turn-off either too late or too early. Both effects may be detrimental and affect the performance of the rectifier. Either they result in the reverse current flow that may cause an efficiency drop or the conduction time of diodes may be reduced.

To keep power conversion efficiency high, several techniques can be utilized to compensate for the propagation delays. A constant offset can be introduced at the comparator input using the unbalanced-bias scheme (asymmetrical input transistors) to compensate for the OFF delay. This can partially solve the problem, since the compensation of ON delay is skipped. Off-chip offset calibration can also be utilized. A switched offset biasing scheme can explicitly control the reverse bias current. In many embodiments, an off-chip calibration method can be utilized. However, problems with these approaches are that they are not flexible due to various reasons (e.g., PVT variations, transistor mismatch, offset, among various others). These schemes can be optimized for the particular operational condition, and their design procedure can be complicated. A near-optimum approach that does not incorporate an ALC unit and PMOS active diode calibration can also be utilized. However, without ALC, reaching a steady state and having near-optimum condition is a real challenge.

Figure 6:
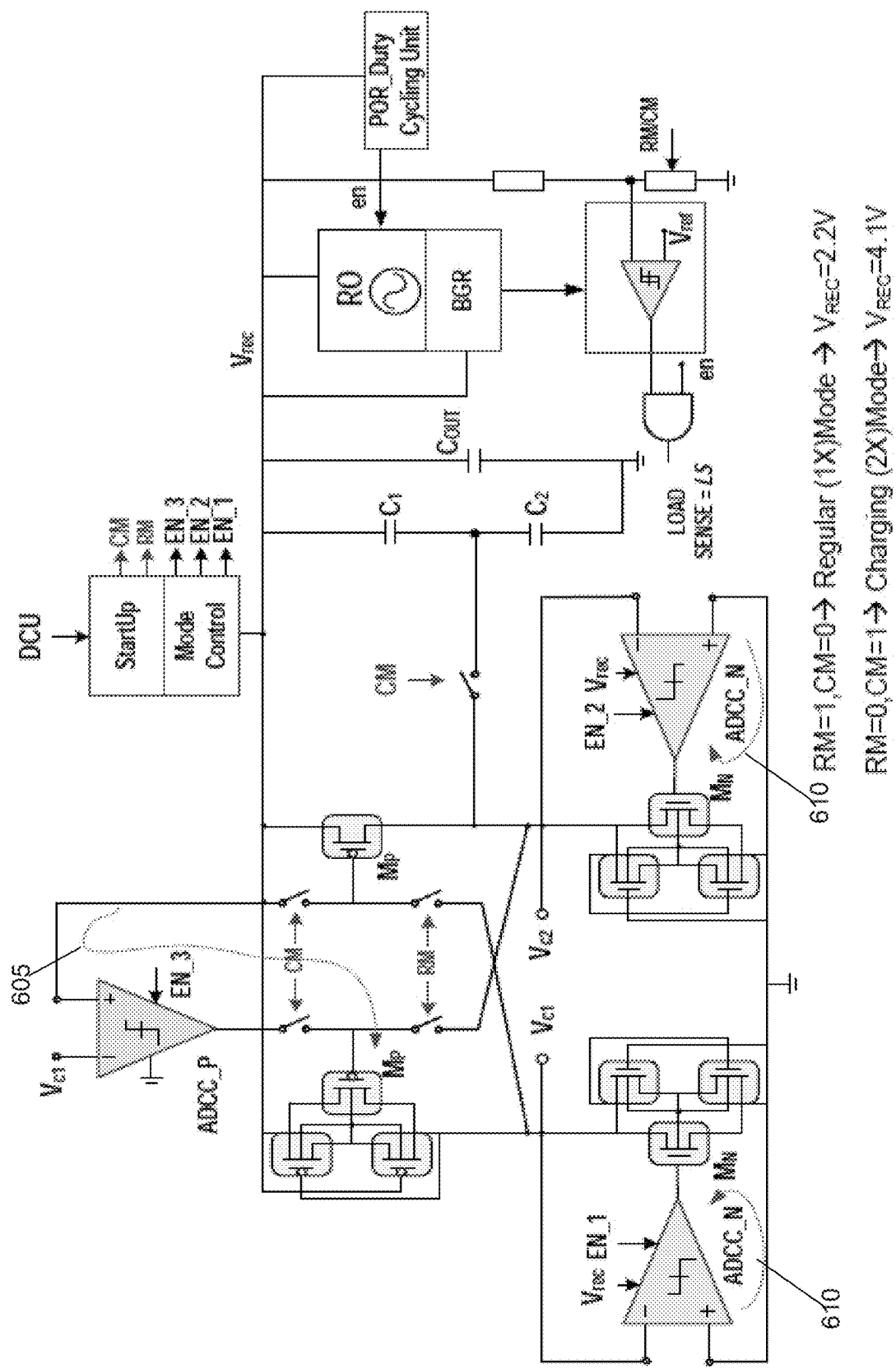
FIG. 6 illustrates a reconfigurable active rectifier for WPT with an ALC unit in accordance with an embodiment of the invention 6.

Accordingly, many embodiments provide a simple architecture that incorporates an adaptive, real-time ON/OFF calibration scheme for both types of active diodes (PMOS, NMOS) that autonomously generates the offset currents for the comparators and is immune to PVT and circuit mismatch. An example of a reconfigurable active rectifier for WPT with an ALC unit in accordance with an embodiment of the invention is illustrated in FIG. 6. In particular, FIG. 6 illustrates an overall AR-WPT architecture capable of working in Regular ($V_{REC}$=2.2V) and Charging ($V_{REC}$=4.1V) Mode with an ALC Unit with complete Calibration Schemes that do not need any tuning.

As illustrated in FIG. 6, AR-WPT includes five power switches, three adaptive delay compensated comparators (two of them for driving the N-type diode and one for driving the P-type diode), duty-cycling control unit for output regulation along with startup and mode control units. Depending on the states of these five switches, the AR-WPT can be configured to work in the following modes:

Regular Mode, where RM switches are turned-on and MP transistors are cross-connected with the gate of one connected to the drain of another. N-type Active Diodes are enabled, while P-type diode is disabled; and Charging Mode, where RM switches are turned-off and CM-switches are turned-on. CMP1 and CMP3 are enabled. In the steady state, voltage $V_{ac2}$ (one side of secondary coil) is clamped at $V_{REC}/2$, so MP2 is reversed bias and consequently turned-off The lines 605 and 610 show the paths where the delays may be introduced by the comparators. Although FIG. 6 illustrates a particular architecture for a reconfigurable active rectifier for WPT with an ALC unit, any of a variety of architectures may be utilized as appropriate to the requirements of specific applications in accordance with embodiments of the invention.

Figure 7:
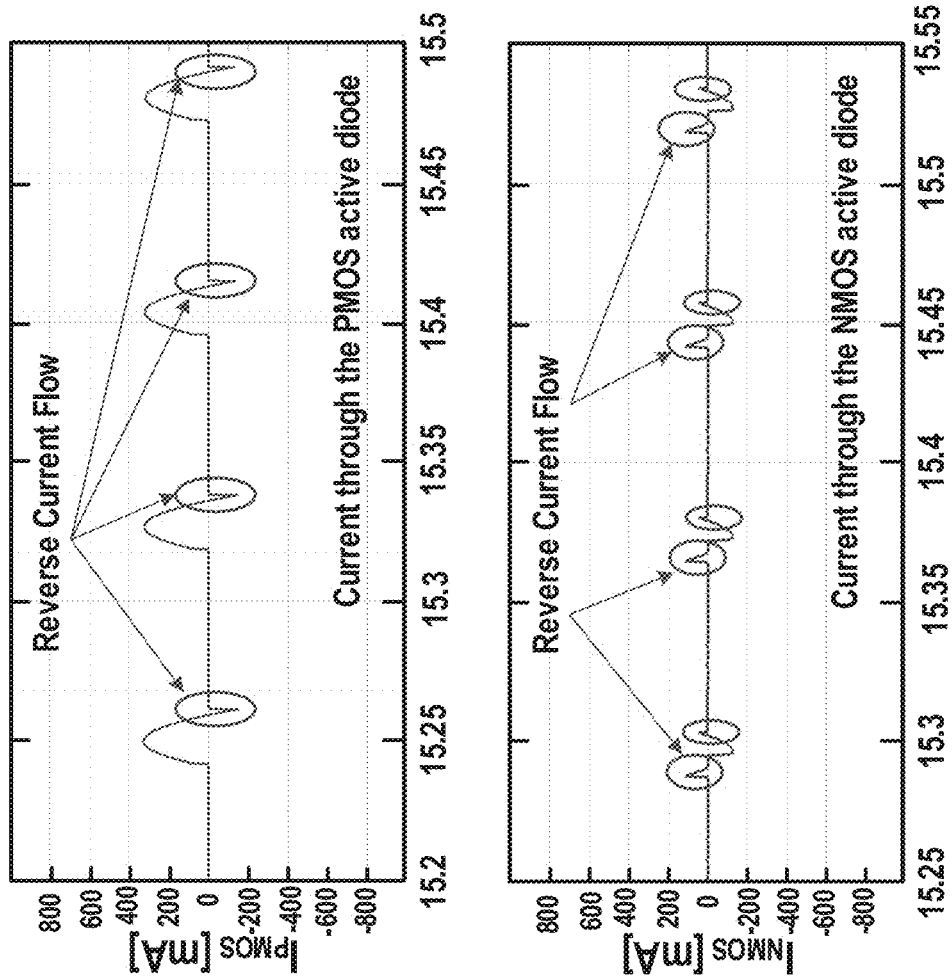
FIG. 7 illustrates impacts of ON and OFF delays for both types of active diodes (AD) without calibration schemes implemented in accordance with an embodiment of the invention

The impact of delays can be multifold. FIG. 7 illustrates impacts of ON and OFF delays for both type of active diodes (AD) without calibration schemes implemented in accordance with an embodiment of the invention.

Figure 8:
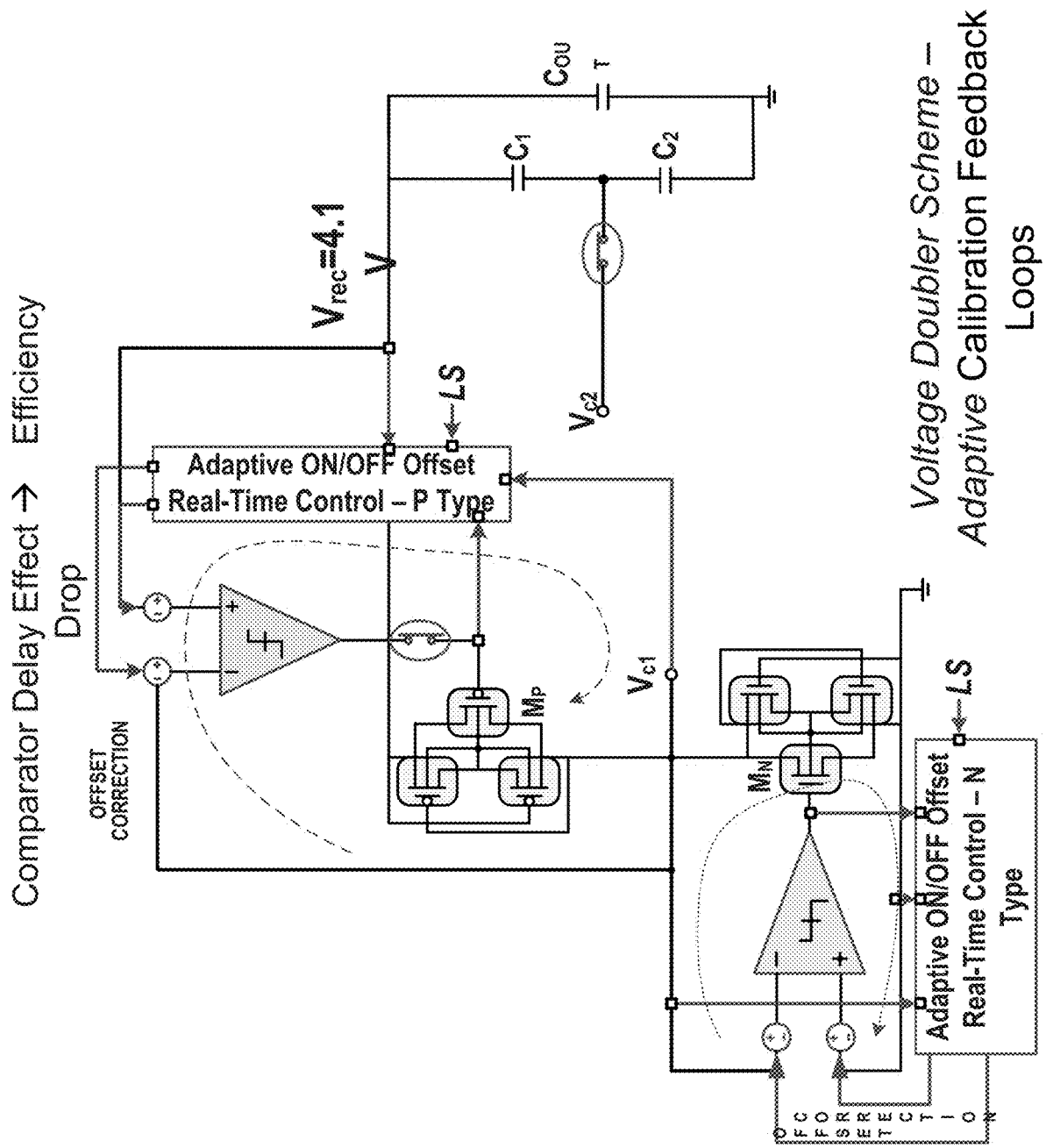
FIG. 8 illustrates block diagrams of a near-optimum active rectifier in charging mode with negative feedback loops for a real-time delay calibration for both N-type and P-type turn-on & turn-off delay compensation in accordance with an embodiment of the invention.
Figure 9:
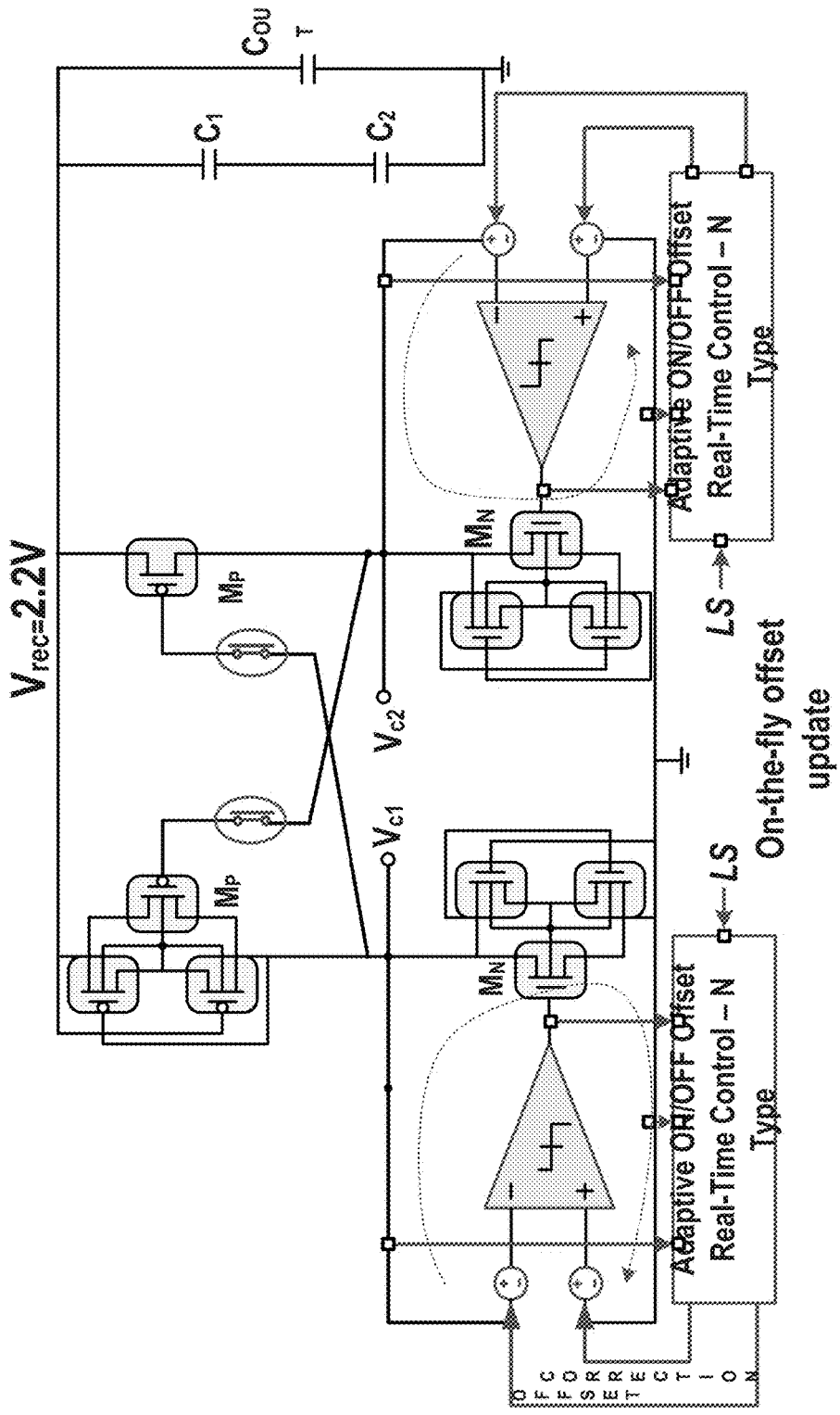
FIG. 9 illustrates block diagrams of a near-optimum active rectifier in regular mode with negative feedback loops for a real-time delay calibration for both N-type and P-type turn-on & turn-off delay compensation in accordance with an embodiment of the invention.

FIG. 8 and FIG. 9 illustrate block diagrams of a near-optimum active rectifier in 1×/2× mode with negative feedback loops for a real-time delay calibration for both N-type and P-type turn-on & turn-off delay compensation in accordance with an embodiment of the invention. These feedbacks can be responsible for adaptive generation of the ON/OFF offset currents to compensate the switch delays. The signals $V_{C1}$, $V_{REC}$ and $V_{GP}$ may be used as an input for the P-type calibration scheme, since they contain the information whether the P-type active diode turned-on/off too early/late or if it is close to the optimum timing. Similarly, the signals gnd, $V_{C1}$ and $V_{GN}$ can be used for the N-type calibration scheme and derivation of the calibration criteria.

Figure 10:
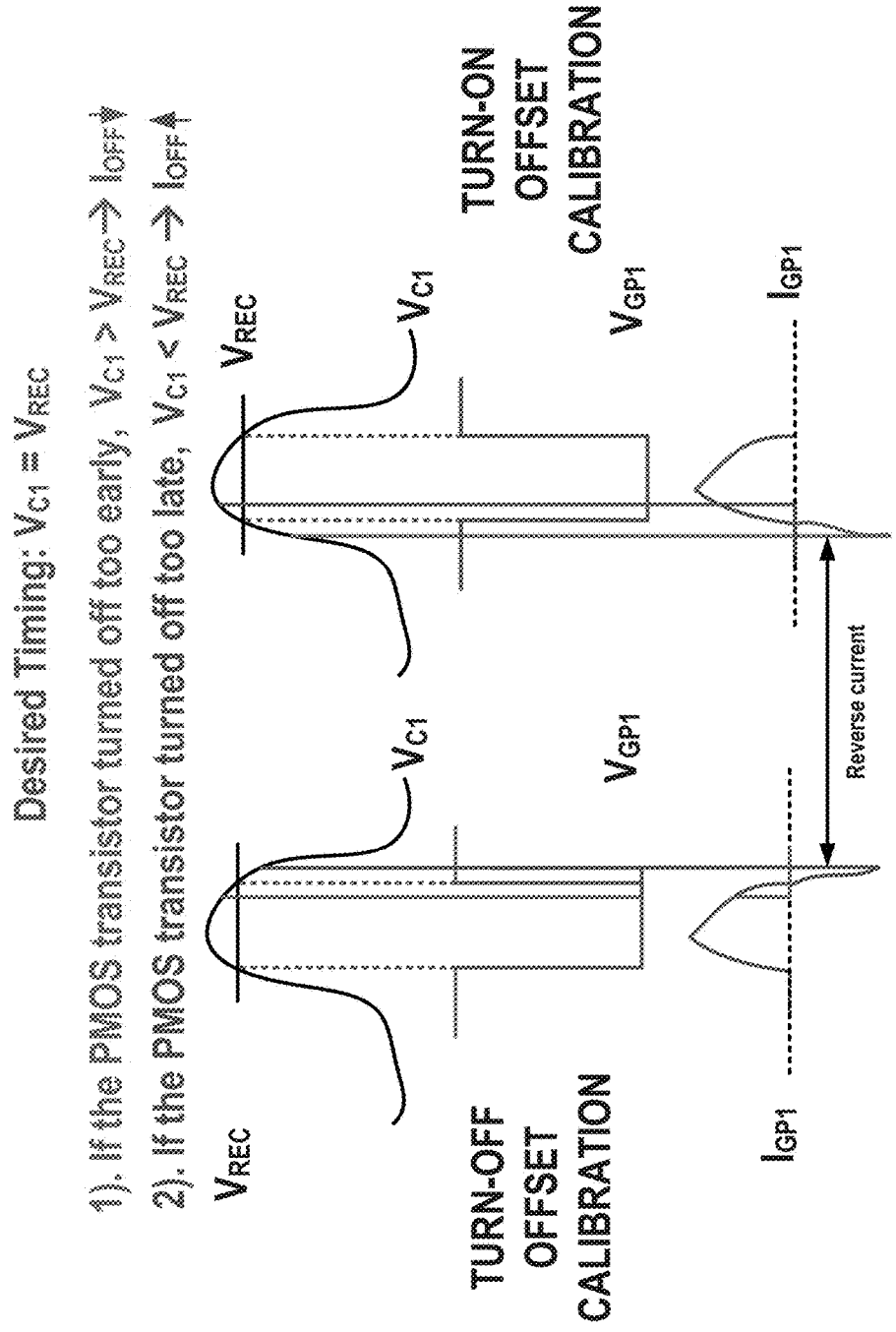
FIG. 10 illustrates calibration criteria for PMOS active diode in accordance with an embodiment of the invention.
Figure 11:
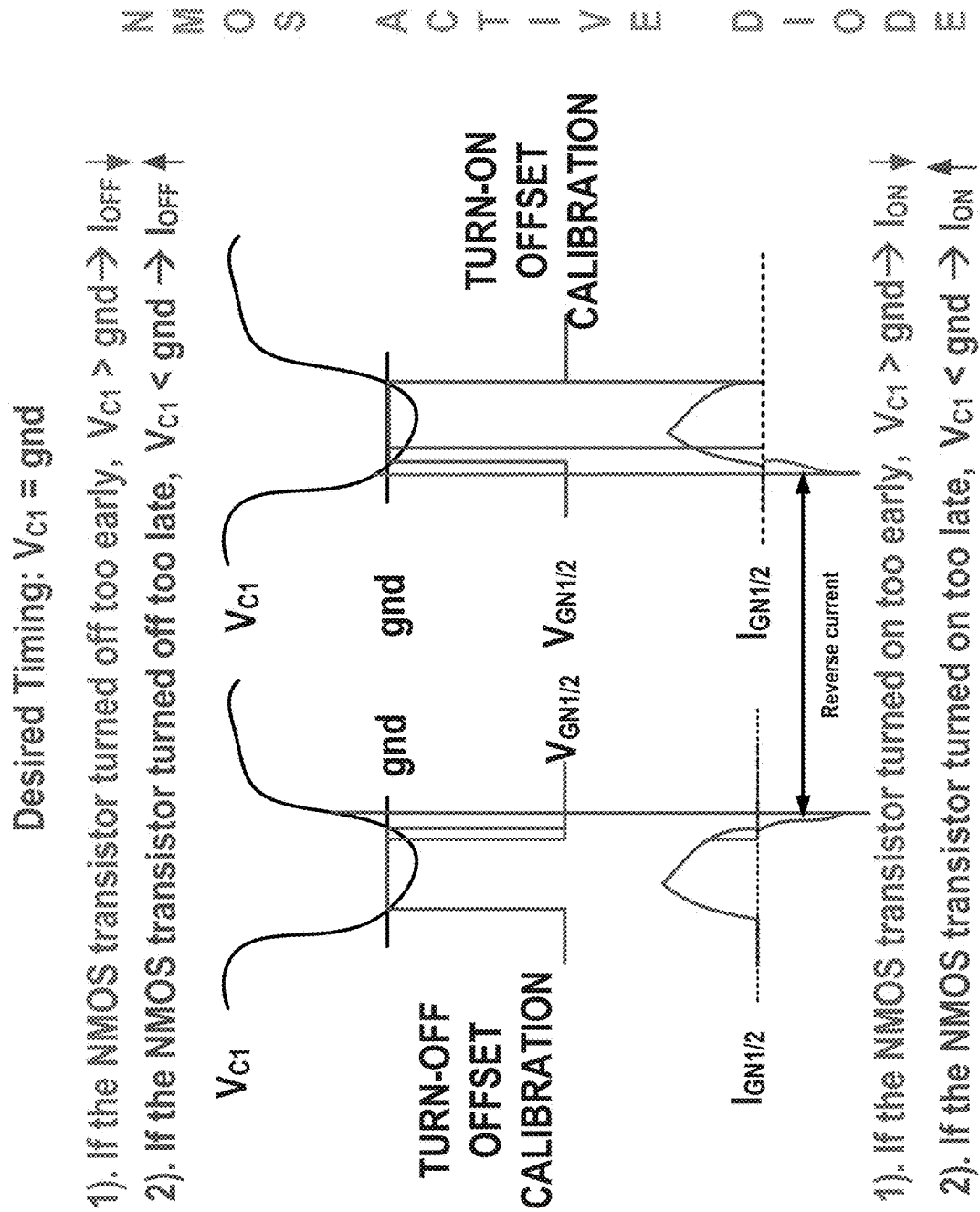
FIG. 11 illustrates calibration criteria for an NMOS active diode in accordance with an embodiment of the invention.

Calibration criteria for both type of active diodes in accordance with an embodiment of the invention is illustrated in FIG. 10 and FIG. 11. Considering an optimum timing for the P-type active diode. A similar analogy can be made for the N-type of active diode with different desired timing criteria. As illustrated in FIG. 10, if a PMOS power transistor is turned-off too early (green line), conduction time is reduced, which means that $V_{C1}$>$V_{REC}$. To fix this, in the next cycle, more offset current through the off-branches in comparator may need to be added. In the analog manner, if a PMOS power transistor is turned-off too late, a reverse current flow is likely to be the result. To reduce this in the next cycle, the offset current through the off-branches should be decreased. Deriving the conclusions for the turn-on offset calibration is done in a similar way. So the offset is updated in every cycle and within several cycles the desired timing condition is reached. In the steady state, if the input signals $V_{C1}$ and $V_{REC}$ are sampled on the rising and the falling edge of the $V_{GP}$, the sampled values should be equal. That implies that delays are fully-compensated. For the N-type of active diode, if the input signal $V_{C1}$ is sampled on the rising and the falling edge of $V_{GN}$, the sampled value should be equal to gnd.

Figure 12:
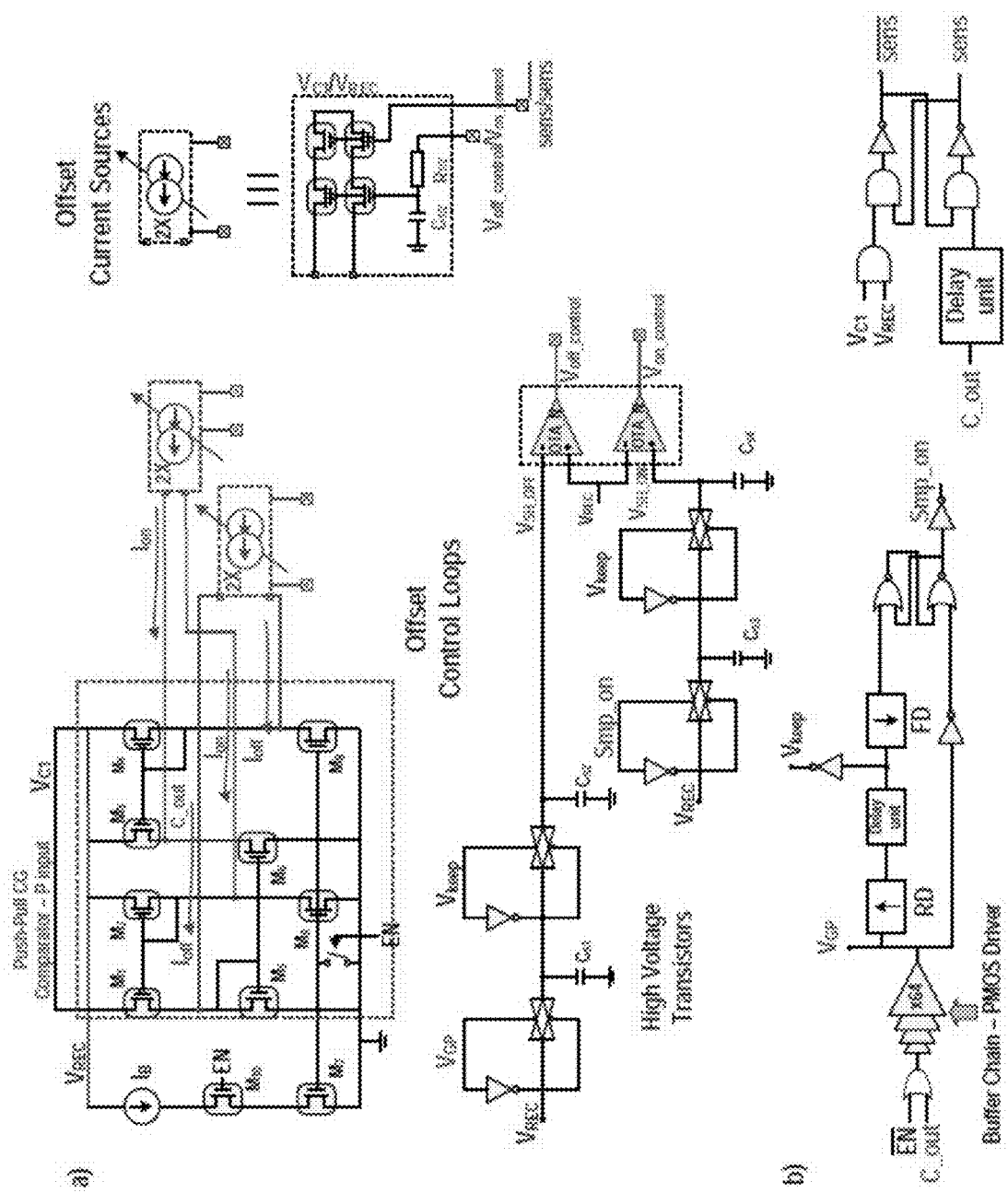
FIG. 12 illustrates a detailed schematic of a real-time, adaptive on/off delay compensation technique for a PMOS active diode in accordance with an embodiment of the invention.
Figure 13:
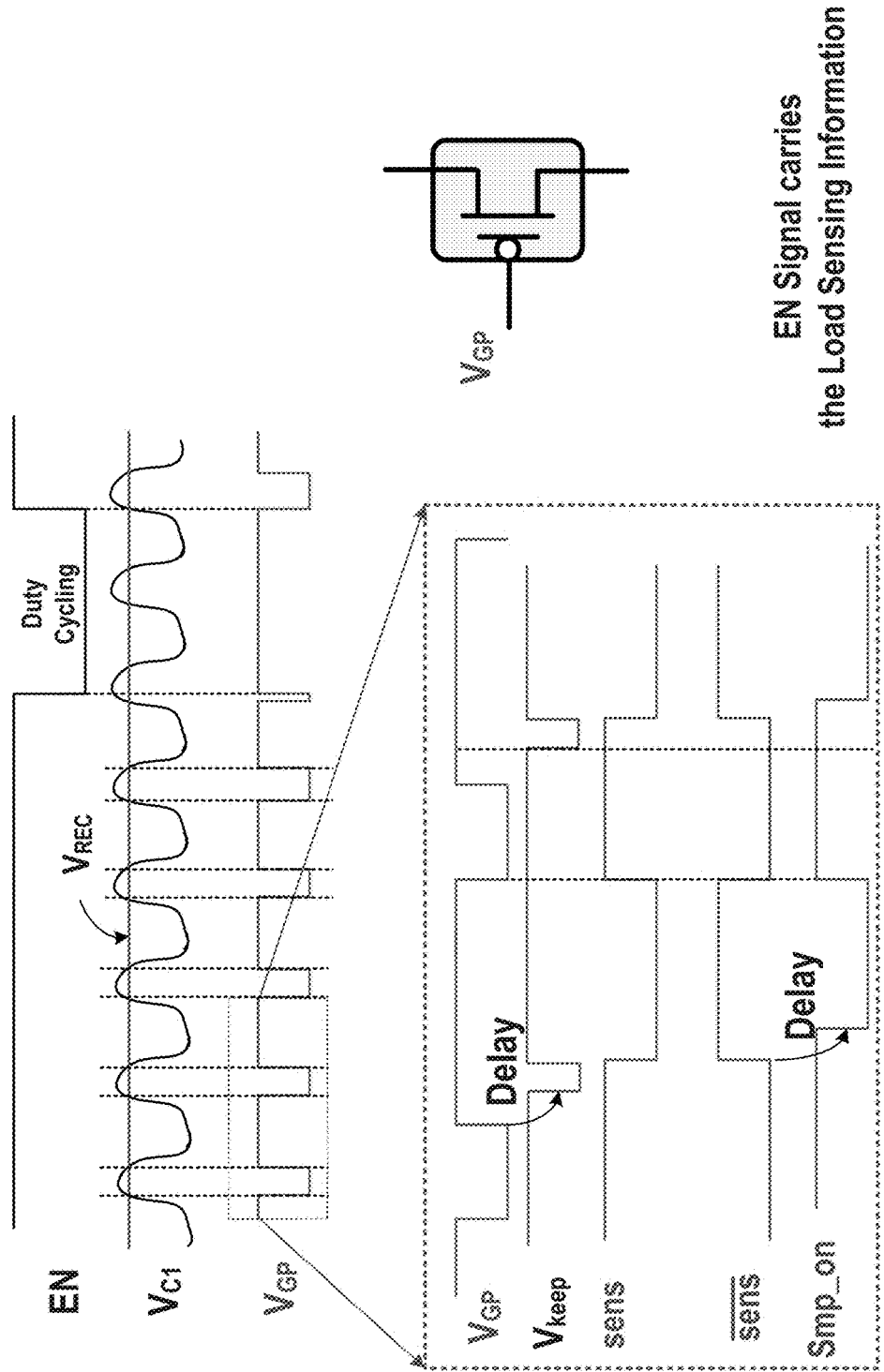
FIG. 13 illustrates a timing diagram for a PMOS active diode driver in accordance with an embodiment of the invention

Detail circuitry of a real-time offset compensation scheme for a P-type active diode in accordance with an embodiment of the invention is illustrated in FIG. 12 and FIG. 13. In particular, FIG. 12 illustrates a detailed schematic of a real-time, adaptive on/off delay compensation technique for a PMOS active diode in accordance with an embodiment of the invention. FIG. 13 illustrates a timing diagram for a PMOS active diode driver in accordance with an embodiment of the invention. Although FIG. 12 illustrates a particular architecture for real-time, adaptive on/off delay compensation technique for a PMOS active diode, any of a variety of architectures may be utilized as appropriate to the requirements of specific applications in accordance with embodiments of the invention.

Figure 14:
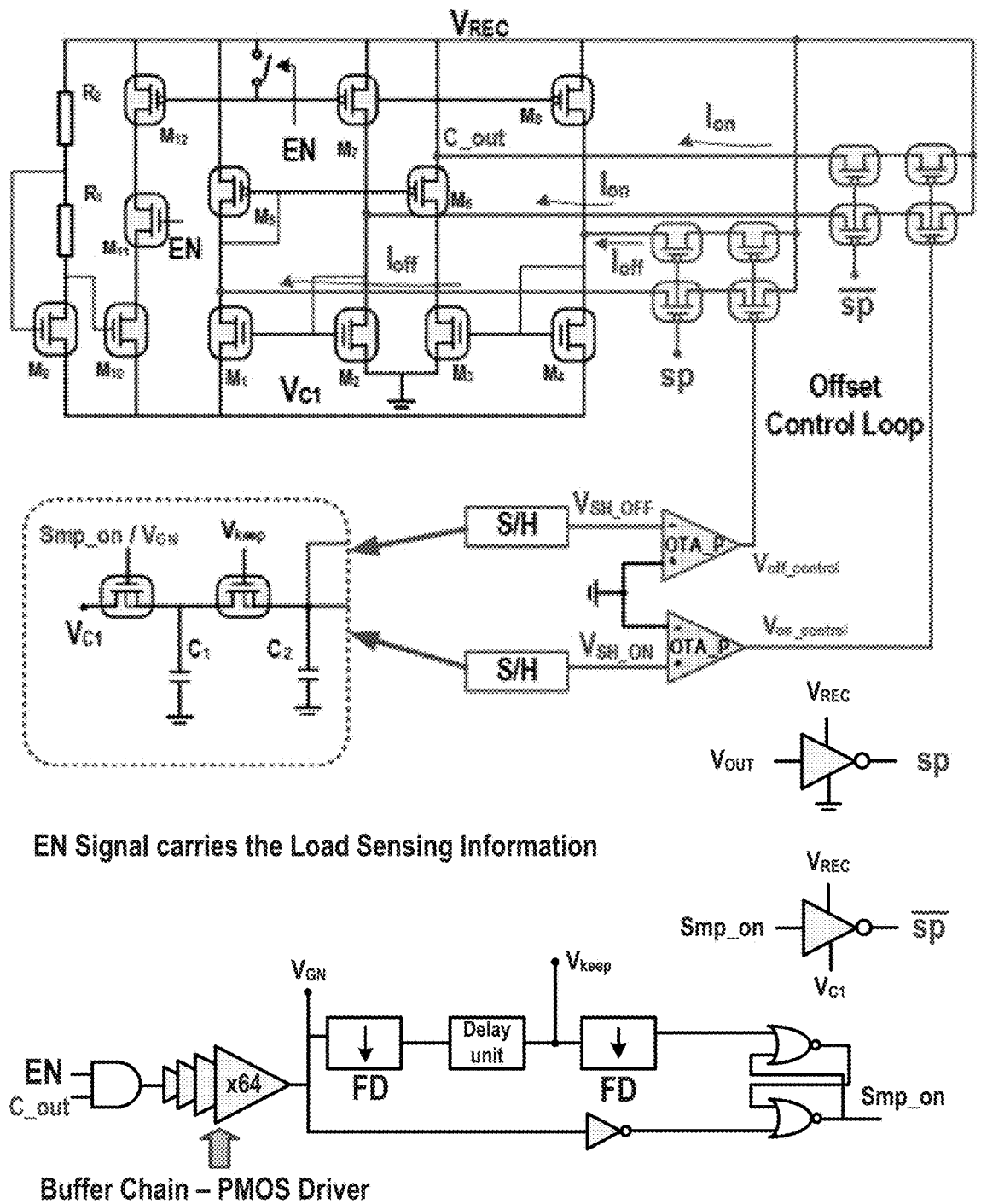
FIG. 14 illustrates a detailed architecture of a real-time, adaptive on/off delay compensation technique for an NMOS active diode in accordance with an embodiment of the invention.
Figure 15:
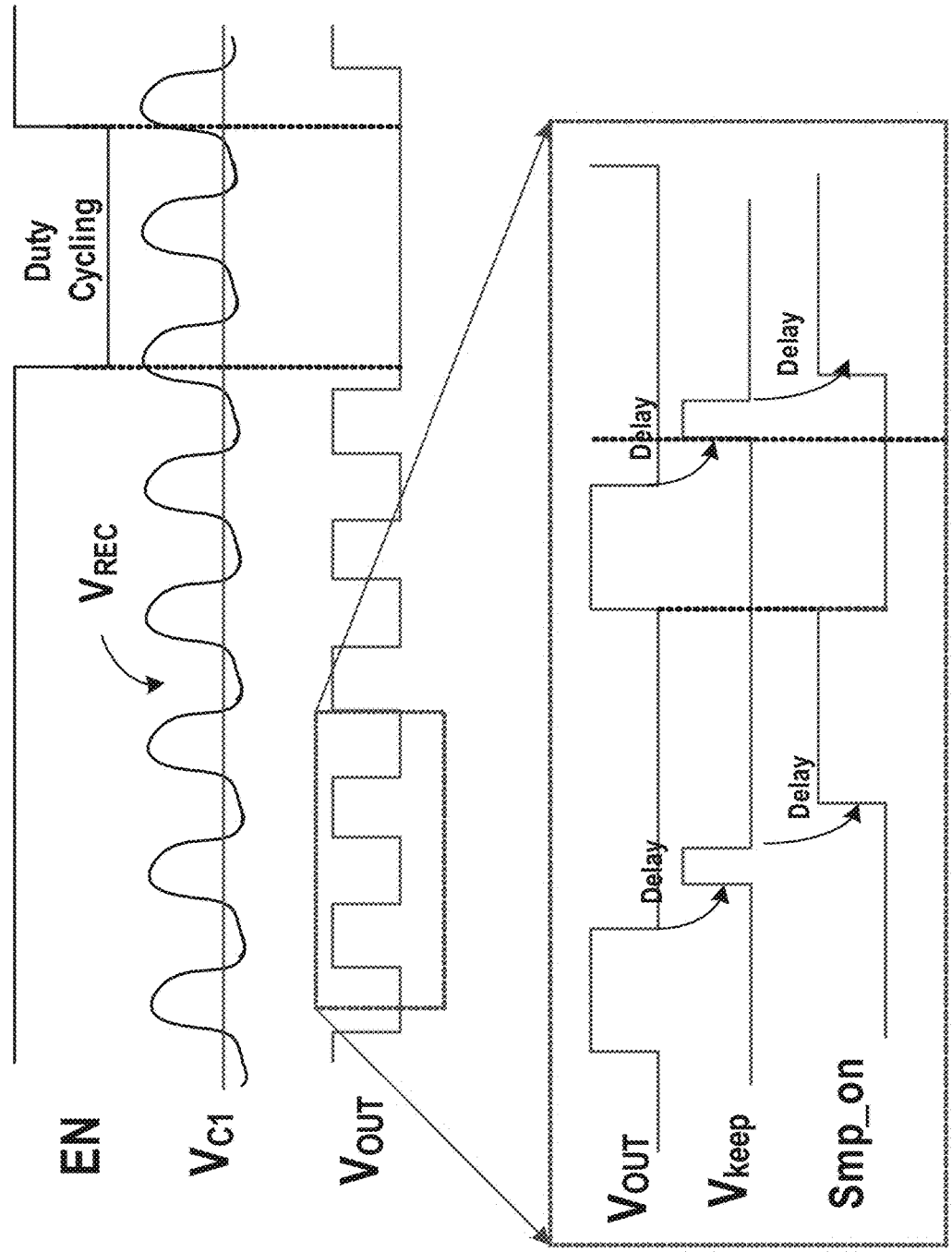
FIG. 15 illustrates a timing diagram for an NMOS active diode driver in accordance with an embodiment of the invention.

In many embodiments, an N-type scheme is represented by a dual circuit and the analysis is similar. A detailed architecture of a real-time, adaptive on/off delay compensation technique for an NMOS active diode in accordance with an embodiment of the invention is illustrated in FIG. 14. A timing diagram for an NMOS active diode driver in accordance with an embodiment of the invention is illustrated in FIG. 15. High voltage transistors may be used in the implementation since AR-WPT can support doubling mode and the range of voltages may go up to 5V. Although FIG. 14 illustrates a particular architecture of an NMOS active diode, any of a variety of architectures may be utilized as appropriate to the requirements of specific applications in accordance with embodiments of the invention.

In many embodiments, in the core of the calibration scheme is the push-pull common gate comparator with the P-input transistors ($M_1$-$M_{10}$). Two negative feedback loops may be added to adaptively generate ON/OFF offset currents. In many embodiments, every feedback loop includes an offset current source, feedback amplifier and the sampling circuitry that plays the role in the ON/OFF timing adjustment.

Figure 16:
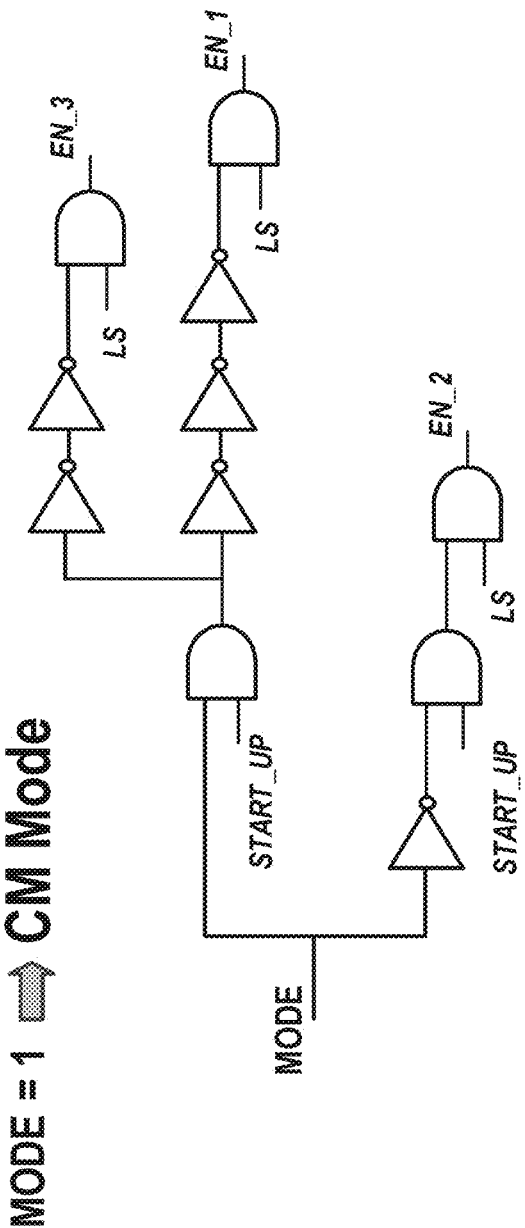
FIG. 16 illustrates control logic for an AR-WPT reconfigurable system in accordance with an embodiment of the invention.

A control logic for an AR-WPT reconfigurable system in accordance with an embodiment of the invention is illustrated in FIG. 16.

Consider an ON-delay compensation path: The control logic may generate signals sens, $\overline{\text{sens}}$, $V_{KEEP}$ and Smp_on. On the rising edge of Smp_on, input voltage $V_{C1}$ may be sampled on $C_{s1}$. During the $V_{keep}$ that voltage value can be passed onto $C_{s2}$ and the feedback amplifier OTA_N can compare the sampled value with $V_{REC}$ until the next falling edge of Smp_on. There may be two possible scenarios: 1) if sampled voltage is smaller than $V_{REC}$, OTA_N will drive $V_{on\_control}$ to the lower value and more offset current $I_{ON}$ is pushed through the stacked PMOS current source. Consequently, the PMOS diode (switch) may turn on later compared to the previous cycle; 2) If sampled voltage is higher than $V_{REC}$, OTA_N will drive $V_{on\_control}$ to the higher value and less offset current $I_{ON}$ is pushed through the stacked PMOS current source. In this scenario, the PMOS diode (switch) may turn on earlier compared to the previous cycle, and as a result, after several 10's of cycles the system may reach a steady state; $V_{SH\_ON}$ should be equal or close to $V_{REC}$ indicating the desired optimal timing. In many embodiments, OFF-compensation path is realized and analyzed in the similar manner—in steady state $V_{SH\_OFF} \approx V_{REC}$. Feedback amplifiers, OTA_N can be realized as the low power folded cascode amplifiers with N-type input transistors and GBW<0.5 MHz.

In several embodiments, to ensure no oscillation and smooth transition between transistor ON/OFF states, RC time delays are added. These delays may behave also as low-pass filters whereby they remove high-frequency components in the offset currents.

Figure 17:
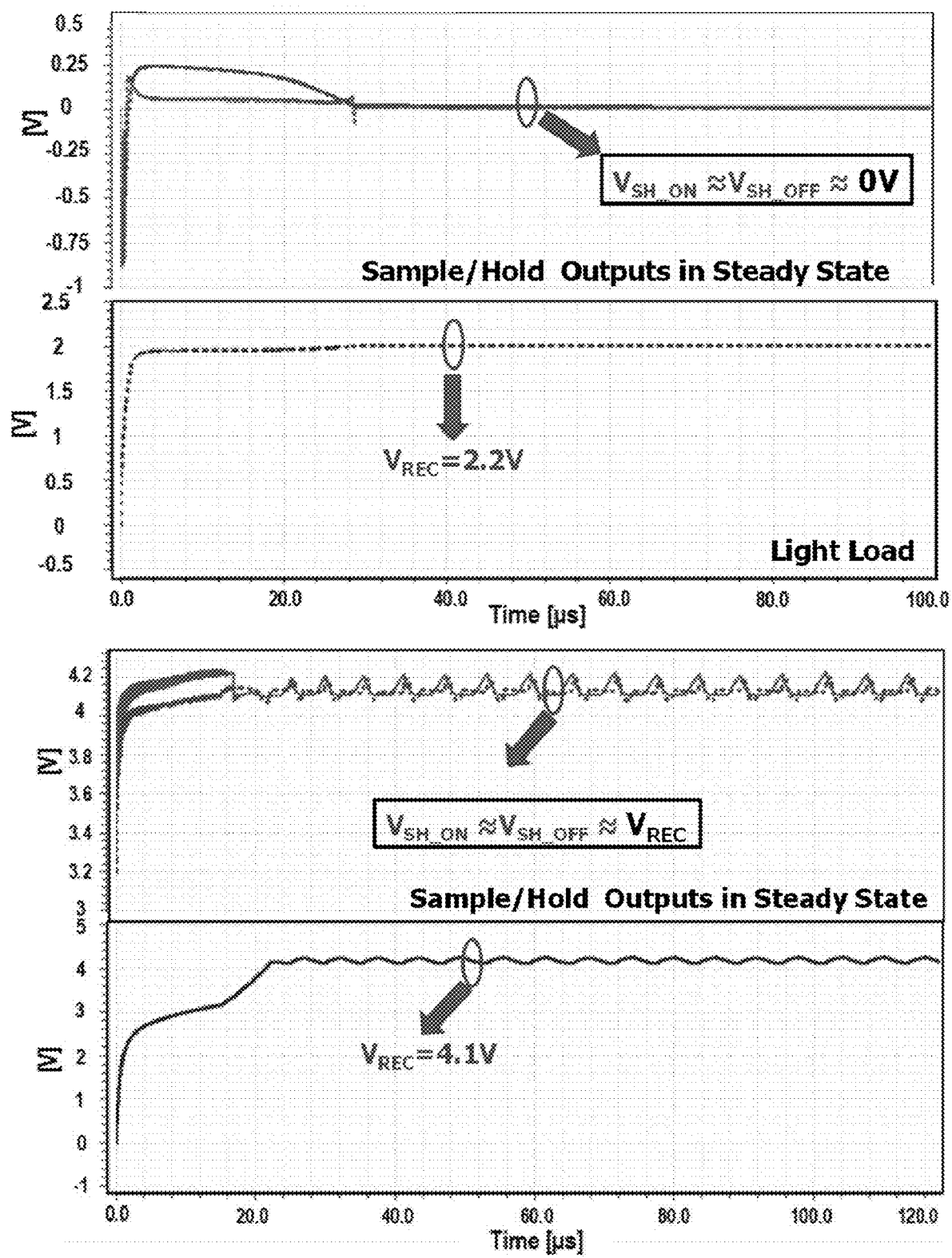
FIG. 17 illustrates near-optimum steady-state operation for both PMOS and NMOS types of diodes in accordance with an embodiment of the invention.
Figure 18:
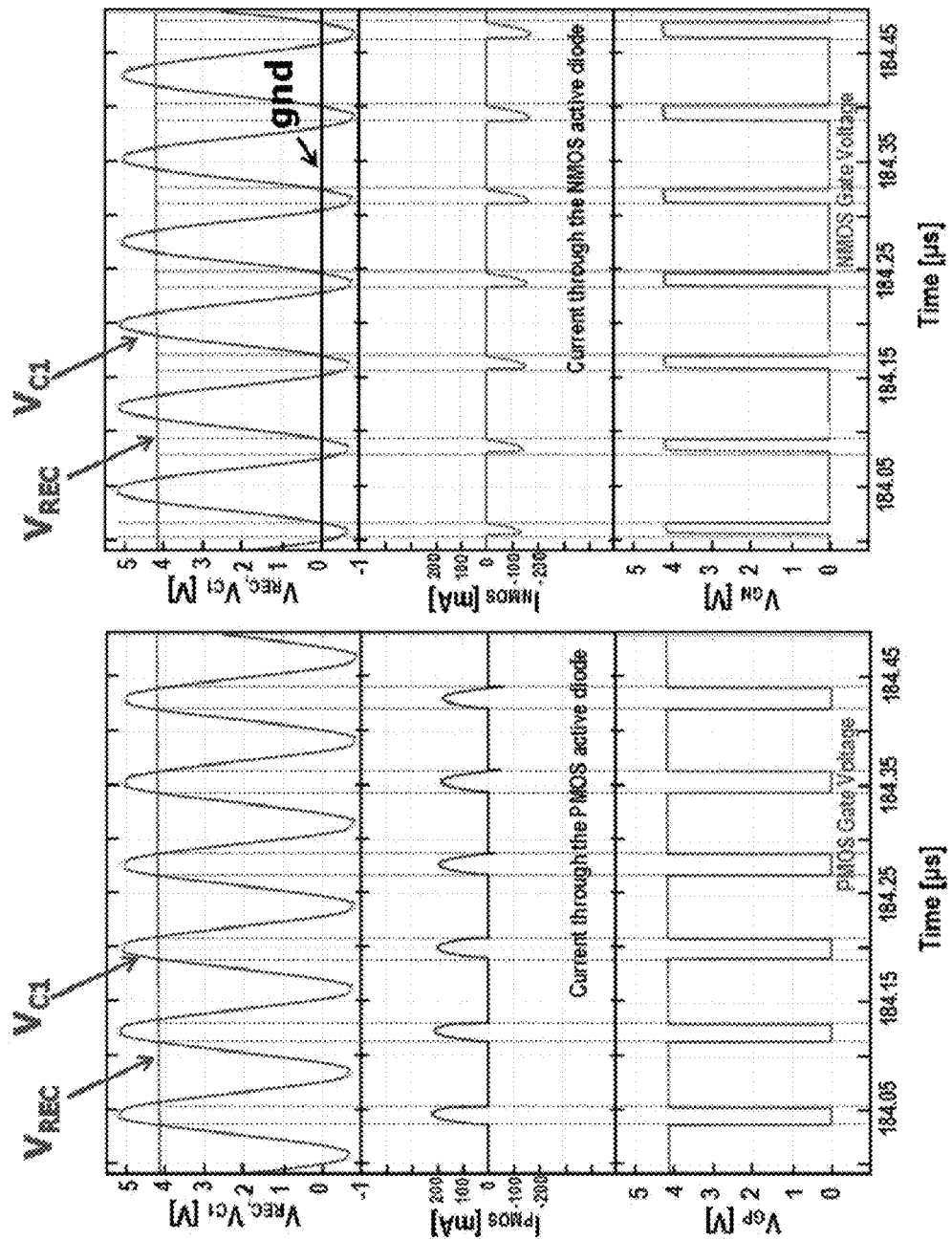
FIG. 18 illustrates relevant waveforms for both modes of operations for a PMOS active diode in accordance with an embodiment of the invention.
Figure 19:
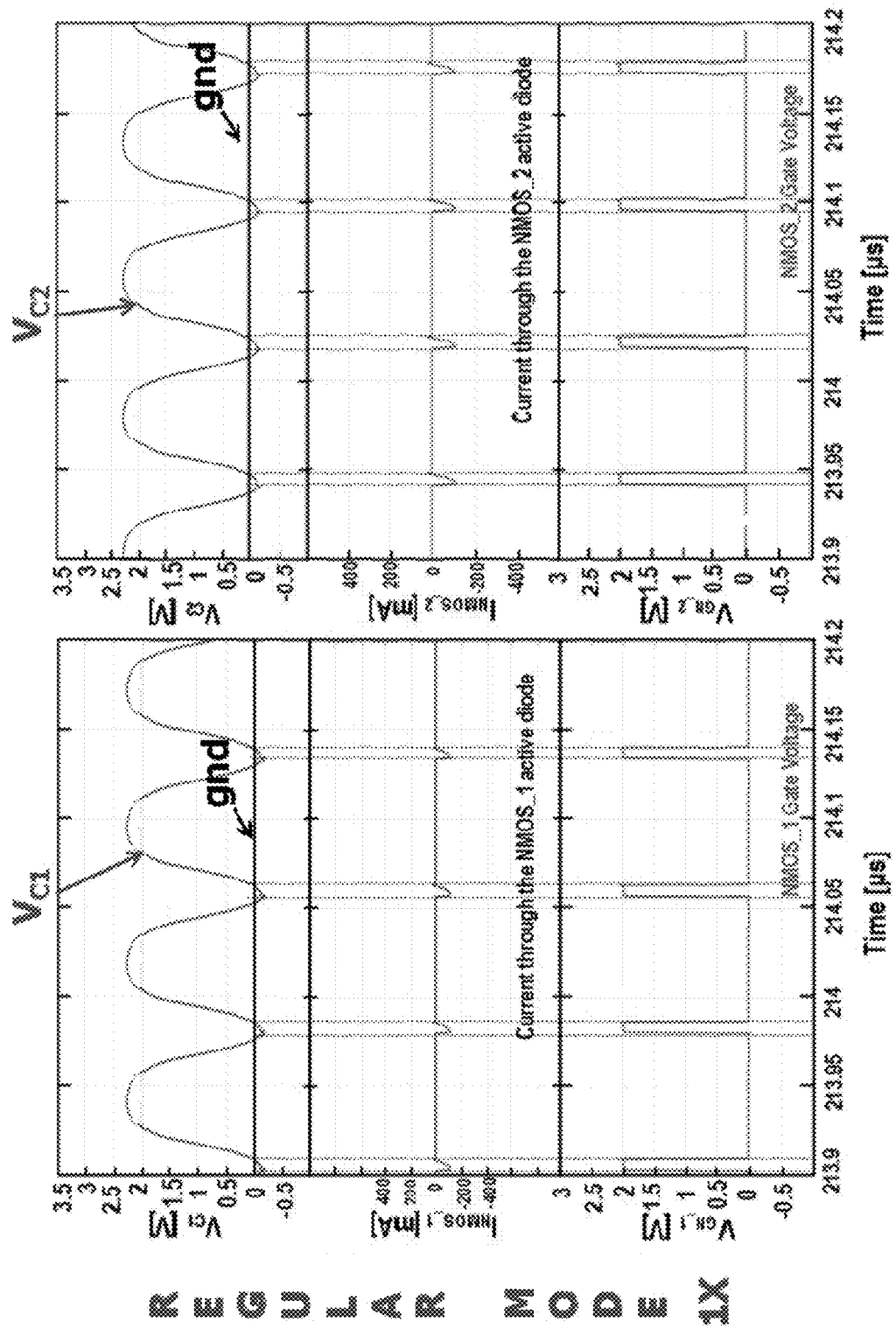
FIG. 19 illustrates relevant waveforms for both modes of operations for an NMOS active diode in accordance with an embodiment of the invention.

In many embodiments, an advantage of the real-time adaptive compensation scheme is its immunity to process mismatch and PVT variations. FIG. 17 verifies the near-optimum steady-state operation for both PMOS and NMOS types of diodes in accordance with an embodiment of the invention. In several embodiments, the outputs of sampling circuit $V_{SH\_ON}$ and $V_{SH\_OFF}$ follow the rectified voltage $V_{REC}$ and gnd for 2× and 1× mode respectively. The relevant waveforms for both modes of operations in accordance with an embodiment of the invention are illustrated in FIG. 18 and FIG. 19. This demonstrates the effectiveness of the illustrated technique—with adaptive ON/OFF compensation scheme implemented, the system reaches the desired optimum timing and the effect of reverse current and reduced conduction time (which affect the efficiency) are eliminated or significantly mitigated.

Figure 20:
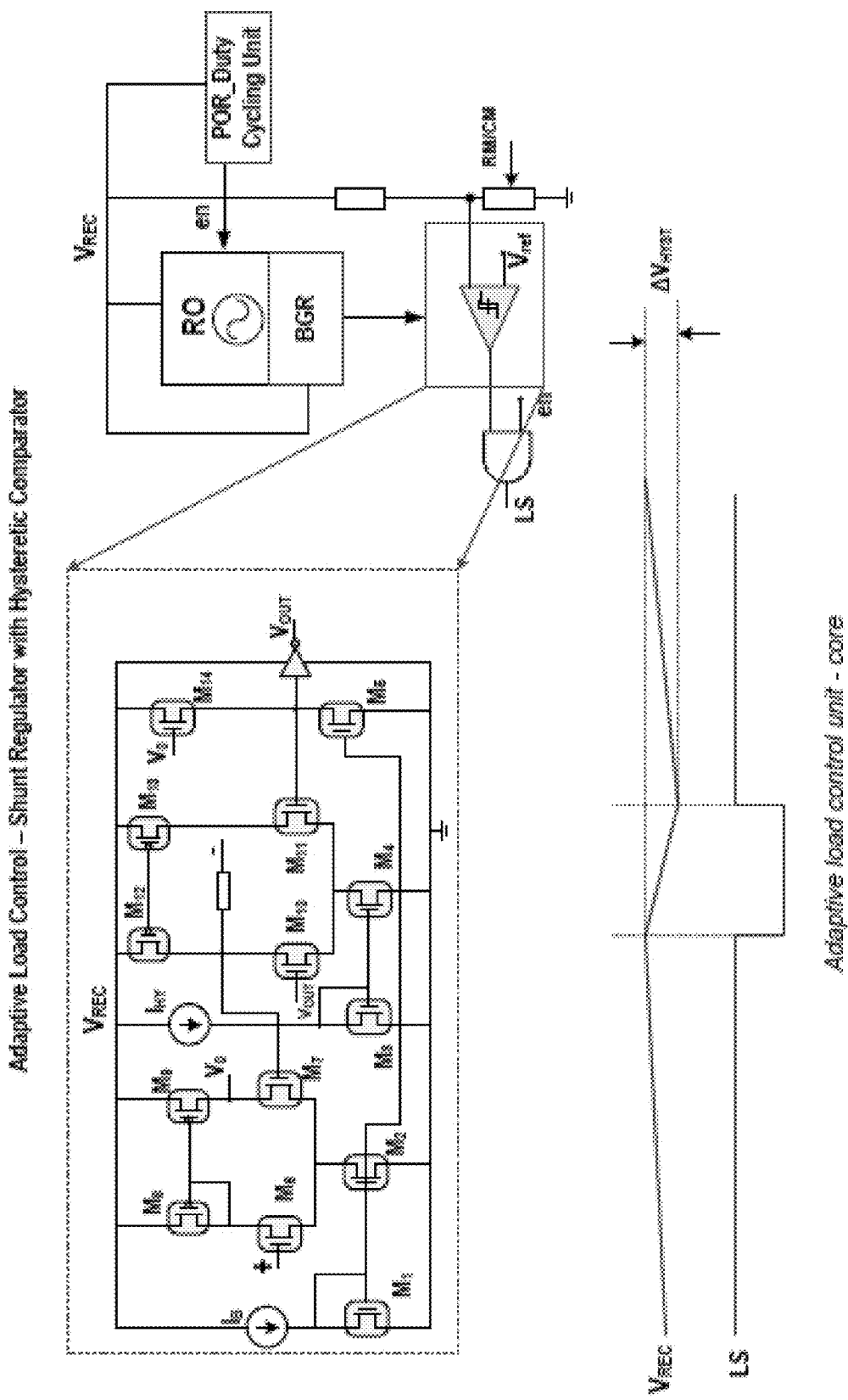
FIG. 20 illustrates an ALC unit incorporating an Hysteretic Comparator (HC) in accordance with an embodiment of the invention.

In many embodiments, since the load requirement varies over time, implementation of an ALC unit is necessary. An ALC unit incorporating an Hysteretic Comparator (HC) in accordance with an embodiment of the invention is illustrated in FIG. 20. As illustrated in FIG. 20, the hysteresis is appended to the 2-stage amplifier by employing a resistor of fixed value together with the steering (current) circuit. This results in the amplifier's negative input terminal being shifted by a value proportional to the product of the resistor and hysteresis bias current. Hysteresis bias current may control the hysteresis properties (e.g., window, slope, among others). In many embodiments, when the output voltage $V_{REC}$ reaches the desired value, the comparator in the feedback circuit will change the value of the control signal LS. As a result, all diodes in the AR-WPT would be turned-off and power transfer from input to output is suspended. In several embodiments, if the hysteresis window is kept at 100 mV, the output voltage $V_{REC}$ will fluctuate within 100 mV window around the desired value. If a regular comparator is used, the hard switching would introduce a sharp voltage ringing observable at the output. This can make the circuit intrinsically unstable. Consequently, the calibration mechanism may not establish the steady state in the rectifier since it may need dozens of cycles. With the inclusion of the hysteretic comparator, the circuit may enter periodically into shut-down (duty cycling) modes, and still have time to calibrate ON/OFF delays in AR-WPT (during LS=0 periods). Load Adaptive signal LS may be coupled into comparator enable signals (EN_1-EN_3). HC may dynamically keep the $V_{REC}$ at the desired level by toggling LS which consequently leads to energy preservation, improving the AR-WPT efficiency and reducing current leakage through the ALC unit.

The discussion thus far has mainly focused on the RX local wireless voltage rectification and regulation. In particular, many embodiments provide circuitry that reduces complexity, utilizes a minimal number of off-chip components and can lead to improved efficiency. However, in many embodiments, a complete wireless power system may also utilize a TX independent IC. Backscattering can be utilized, where TX is driven by the RX as the impedance changes on the receiver side during implant operation. This design typically utilizes an extra off-chip coil. In many embodiments, a TX-RX data link is utilized, so that TX can receive feedback information from the RX unit that contains the sensed loading at the implant side. These systems often incorporate microcontrollers, pulse generators and other off-chip units that can be power hungry. In several instances, the circuitry includes a class D/E power amplifier on the TX side switching at the carrier frequency and driving the inductive link. The power requirements of such amplifiers can be limiting in implant-scale biomedical applications.

Many embodiments provide a new wireless power link architecture that is relatively immune to distance variation and can sense the implant "needs" without explicit feedback from the RX unit. The TX unit together with the link can self-regulate the power delivery to meet implant requirements.

In many embodiments, the idea is that by employing a simple cross-coupled oscillator architecture with automatic amplitude control (AAC), the system in accordance with many embodiments can self-tune to one of two stable frequencies. It can be shown that operation in one of these two frequencies would lead to a constant ratio between the source and load voltages $$V_L/V_S = \sqrt{\frac{L_2}{L_1}},$$

thus making it independent of coupling coefficient and load. This means that a wireless power system can hold the voltage amplitude at remote load constant as load resistance varies.

Battery Charging

In many embodiments, the battery charging (BC) unit accepts an input signal of 4.1V at the input and charges (5-10 mA loading current) a Li-ion battery system with a constant current. In several embodiments, the Li-ion battery requires 3.6V-3.9V for normal operation. As can readily be appreciated, the voltage requirements of a given battery are largely dependent upon the requirements of a particular application. In several embodiments, an integrated buck dc-dc converter steps down the output voltage from the charging unit to 2.2V and is able to provide up to 10 mA of output current. Many embodiments provide a built-in resistance compensator technique that improves the speed of battery charging. This technique dynamically estimates the external resistance of the battery system and extends the phase of the constant-current stage. A smooth transition method can enable stable transition from the Constant-Current to the Constant-Voltage stage for the BC. In the core of the BC, many embodiments provide an LDO-based circuit accompanied with the built-in resistance compensator and the Smooth Control Circuit and that includes Reference Shift Circuit, External Resistance Detector and Reference Voltage Switch.

Simulation and Measurement Results

Figure 21:
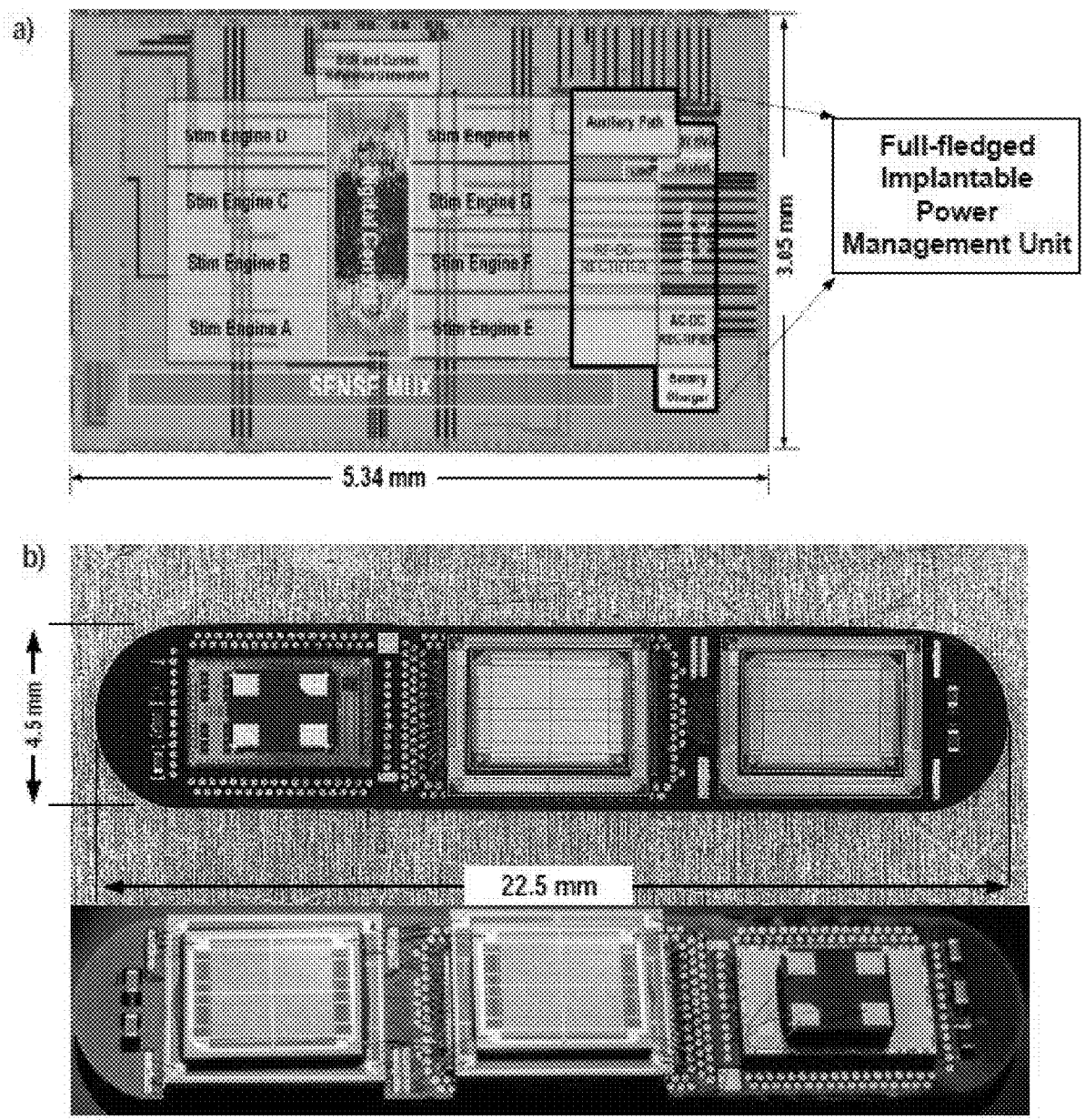
FIG. 21 illustrates a test-bench board and miniaturized neuromodulation (NM) implant board for evaluating the performances of a STIM/PM IC in accordance with an embodiment of the invention.
Figure 22:
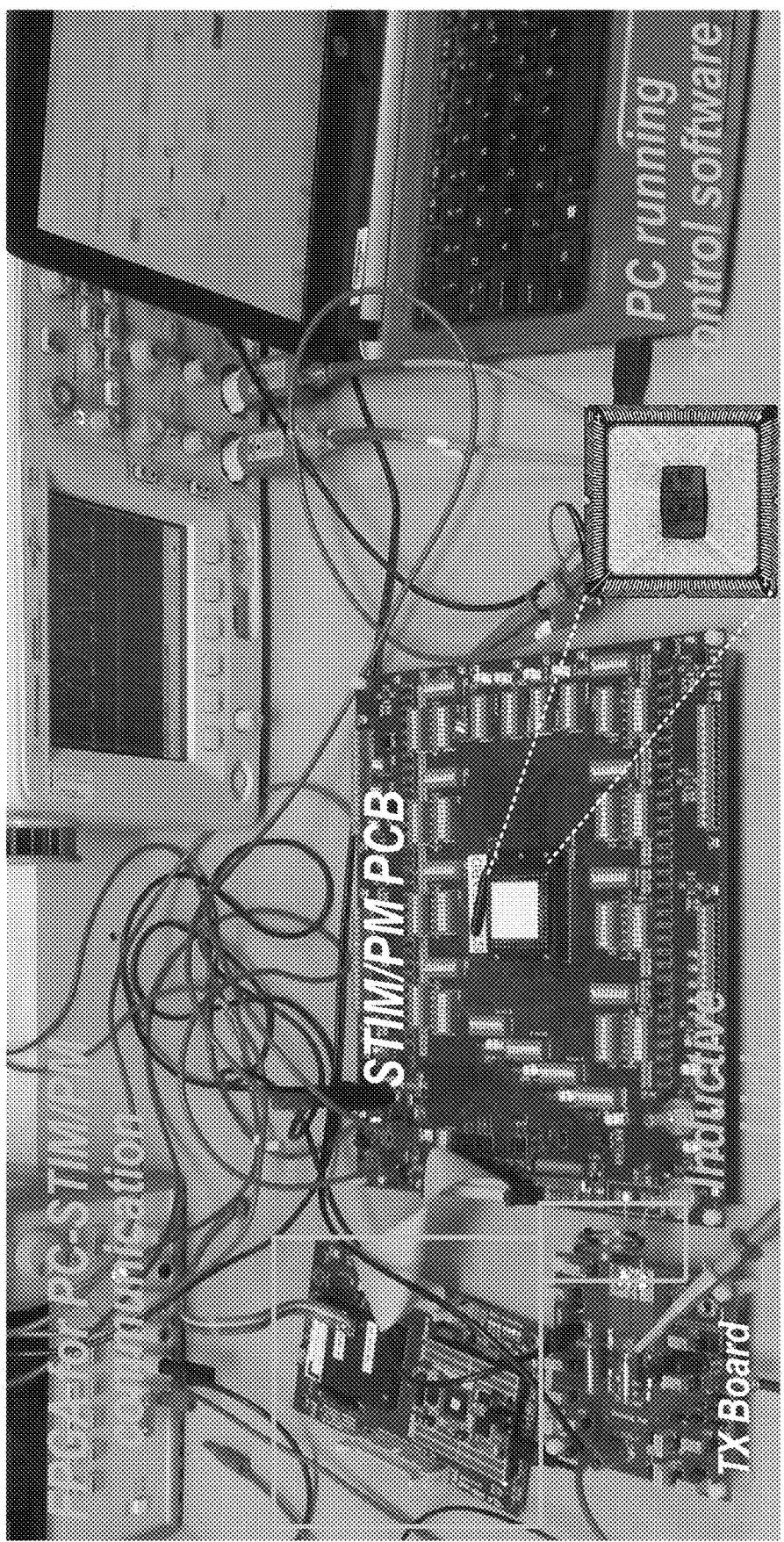
FIG. 22 illustrates a test-bench board and miniaturized neuromodulation (NM) implant board for evaluating the performances of a STIM/PM IC in accordance with an embodiment of the invention.

To evaluate the performances of our STIM/PM IC, a test-bench board and miniaturized neuromodulation (NM) implant board can be constructed that house an IC, as illustrated in FIG. 21 and FIG. 22 in accordance with an embodiment of the invention. The measurement setup may also include a TX board and a wireless inductive link. The TX board can house the transmitter IC with AAC. A PC may be running control software, which sends the control parameters through the FPGA board toward the IC. This setup is primarily used to evaluate the performances of an integrated PM unit, specifically—the reconfigurable ON/OFF delay compensated active rectifier during the operation in 1×/2× mode.

The 13.56 MHz signal can be used for the power carrier frequency during the rectifier's power conversion efficiency (PCE) evaluation while in the overall measurements, the system self-tunes to a frequency in the range 10.5 MHz-13.56 MHz.

Figure 23:
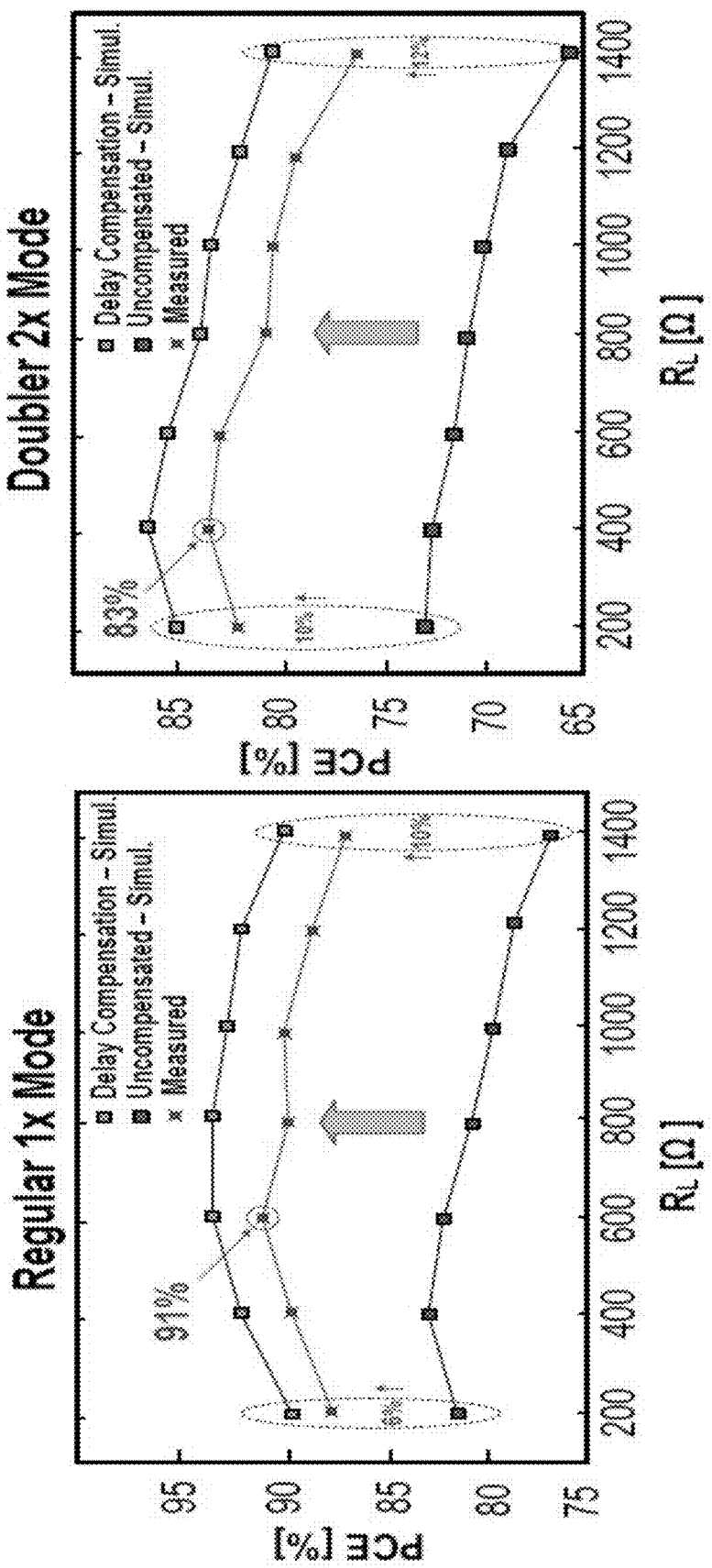
FIG. 23 shows a PCE performance comparison between the delay compensation technique turned-on and turned-off in accordance with an embodiment of the invention.
Figure 24:
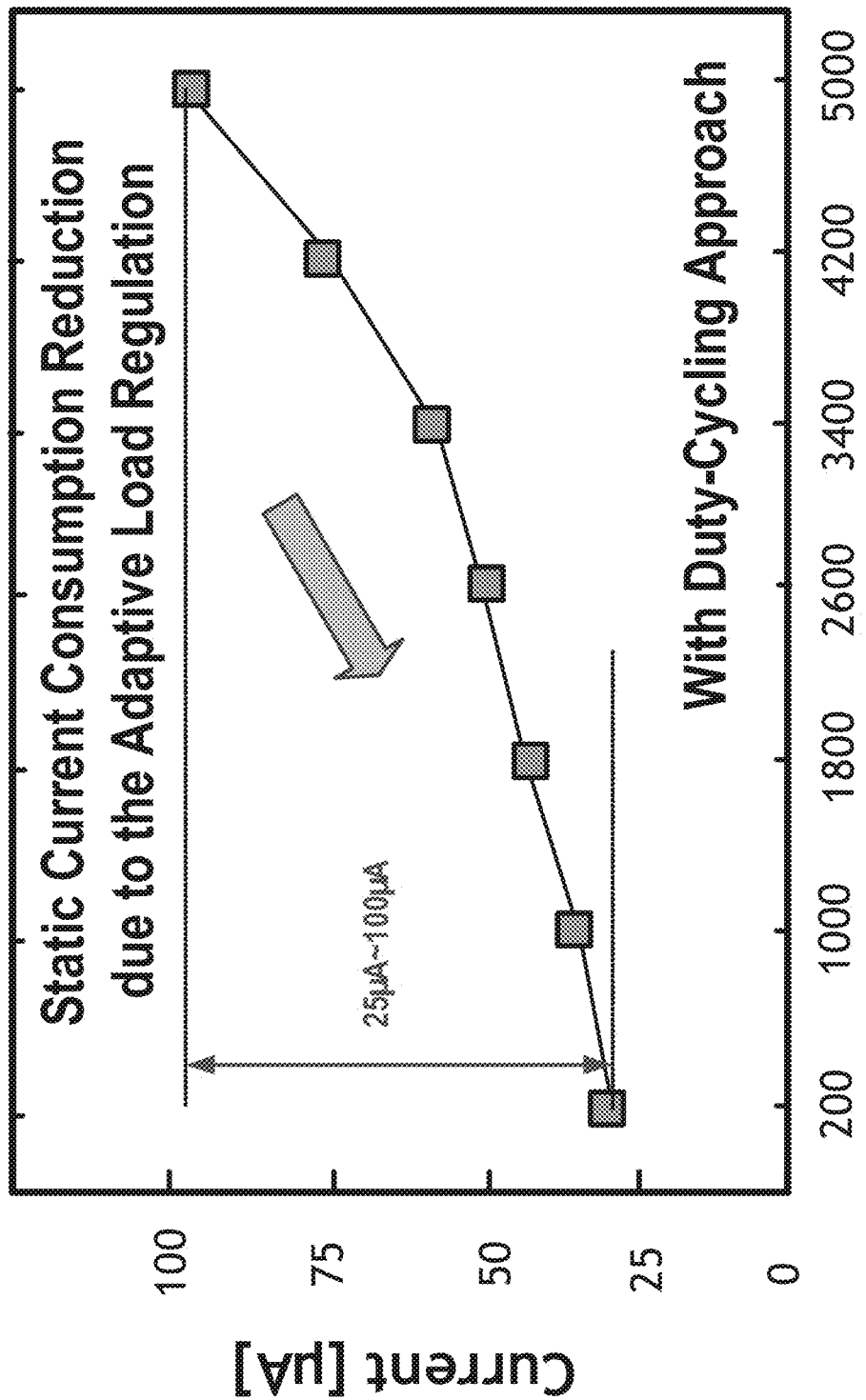
FIG. 24 shows performance of adaptive load control for static current consumption reduction due to adaptive load regulation in accordance with an embodiment of the invention.

FIG. 23 and FIG. 24 show the PCE performance comparison between the delay compensation technique turned-on and turned-off in accordance with an embodiment of the invention. Measured results show that high PCE is maintained over a wide range of output powers. During the Regular (1×) Mode, this approach offers, on average, 8% improvements in PCE with 91% peak efficiency and stays above 87% for most of loading conditions. Measured rectifier's PCE that operates in Charging (2×) Mode shows up to 12% and 10% PCE improvement during light and heavy load, respectively. Measurements clearly show that implemented ON/OFF delay calibration technique is typically more beneficial in eliminating the reverse current flow for lighter loads. This is consistent with the prediction, since the integrated ALC unit is more effective for moderate and small output currents.

Accordingly, many embodiments provide an integrated full-fledged MIMO power management unit that supports different power delivery options, such as wired, wireless and rechargeable battery. This flexibility extends the application range for an NM implant. An adaptive, real-time ON/OFF delay compensation scheme for both N-type and P-type active diodes in an active rectifier, can be implemented. The active rectifier can operate in 1× and 2× mode as a part of a 13.56 MHz wireless power transfer link. Due to the calibration schemes, the circuit delays (propagation delays of gate drivers and comparators) are well compensated across PVT corners and mismatches. Proposed circuit techniques improved the PCE (>90%) across a wide loading range, while increasing the effectiveness of the wireless power link in delivering a stable voltage to the implant across load and coupling variations.

Although specific implementations for an IPMU are discussed above with respect to FIGS. 1-24, any of a variety of implementations utilizing the above discussed techniques can be utilized for an IPMU in accordance with embodiments of the invention. While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. An implant power management unit (IPMU), comprising:
   a plurality of reconfigurable active rectifiers (AR) for power transfer, wherein the plurality of ARs are configurable to operate in a plurality of different modes of operation, wherein the plurality of different modes include a wireless power transfer mode (WPT), a wireline power transfer mode, and a battery power transfer mode;
   wherein the wireline power transfer mode comprises a wireline power delivery unit that accommodates power flow through a differential pair of wires;
   wherein the battery power transfer mode comprises a rechargeable battery processing unit that concurrently enables battery charging while regulating different voltage domains;
   an adaptive load control (ALC) unit that accommodates power delivery with load requirements, wherein the ALC unit is configured to control an AR voltage based upon a desired value;

control circuitry that is configured to sense voltages and that configures the AR to operate in a particular mode of operation;

a feedback circuit that adaptively generates offset current to compensate for switch delays in at least one active NMOS diode; and a feedback circuit that adaptively generates offset current to compensate switch delays in at least one active PMOS diode.

2. The implant power management unit of claim 1, where the control circuitry is configured to enable two half-wave rectifiers connected in series in a charging mode of operation of the AR such that the AR operates as a voltage doubler.

3. The implant power management unit of claim 1, further comprising:

a battery;

wherein the AR comprises a differential AC input;

wherein the charging mode is enabled during recharging of the battery by the IPMU as battery requires a higher input voltage swing than the input voltage swing of an input signal received at the AC input during the regular mode.

4. The implant power management unit of claim 1, wherein the feedback circuit further comprises autonomous feedback that in real-time adaptively generates offset currents and further comprises a comparator that is realized as a push-pull common-gate comparator.

5. The implant power management unit of claim 4, wherein the push-pull common-gate comparator comprises p-type input transistors.

6. The implant power management unit of claim 4, wherein the push-pull common-gate comparator comprises n-type transistors.

7. The implant power management unit of claim 1, wherein the AR comprises a plurality of comparators that drive the gates of power transistors within active diodes.

8. The implant power management unit of claim 7, further comprising an offset calibration circuit configured to generate offset currents for the comparators in the AR.

9. The implant power management unit of claim 8, wherein the AR comprises five power switches, three adaptive delay compensated comparators with two driving an NMOS diode and one driving a PMOS diode.

10. The implant power management unit of claim 1, wherein the ALC unit comprises a Hysteretic Comparator (HC).

11. The implant power management unit of claim 10, wherein the HC is connected to a 2-stage amplifier by employing a resistor of fixed value together with a steering circuit, wherein the amplifier's negative input terminal is shifted by a value proportional to the product of the resistor and a hysteresis bias current output by the HC.

12. The implant power management unit of claim 1, wherein the IPMU operates in the wireline power transfer mode where power is delivered differentially through a plurality of wires.

13. The implant power management unit of claim 1, wherein the IPMU operates in the WPT mode where power is delivered through a near-field inductive link.

14. The implant power management unit of claim 1, wherein the IPMU operates in the WPT mode where power is delivered through an inductive link while simultaneously charging a rechargeable battery.

15. The implant power management unit of claim 1, wherein the IPMU operates in the battery power transfer mode where power is supplied from a battery.

16. The implant power management unit of claim 1, further comprising a scalable bandgap reference current block (BGR/IR) and a plurality of voltage generators for a plurality of implant units.

17. The implant power management unit of claim 1, further comprising two wires at an input that carry sinusoidal signals shifted for 180 degrees such that the net input voltage sum in the two wires is equal to zero.

18. The implant power management unit of claim 1, further comprising a duty-cycle control unit used as a shunt regulator that adapts power delivery to the load and sets the active rectifier output voltage to a desired value.

19. The implant power management unit of claim 1, wherein an active diode inputs two control signals for transitioning from passive to active mode and for preventing excessive power dumping to the load.

20. The implant power management unit of claim 1, further comprising an active body biasing scheme (ABB) that connects the bulk of each power transistor to a higher potential node.

* * * * *